United States Patent
Mitter et al.

(10) Patent No.: US 10,676,743 B2
(45) Date of Patent: Jun. 9, 2020

(54) PLANT-PROTECTING RNAI COMPOSITIONS COMPRISING PLANT-PROTECTING DOUBLE-STRANDED RNA ADSORBED ONTO LAYERED DOUBLE HYDROXIDE PARTICLES

(71) Applicant: THE UNIVERSITY OF QUEENSLAND, St. Lucia, QLD (AU)

(72) Inventors: Neena Mitter, Seventeen Mile Rocks (AU); Zhi Ping Xu, Westlake (AU); Gao Qing Lu, Mt Ommaney (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 15/106,548

(22) PCT Filed: Mar. 14, 2014

(86) PCT No.: PCT/AU2014/000255
§ 371 (c)(1),
(2) Date: Jun. 20, 2016

(87) PCT Pub. No.: WO2015/089543
PCT Pub. Date: Jun. 25, 2015

(65) Prior Publication Data
US 2017/0029819 A1    Feb. 2, 2017

(30) Foreign Application Priority Data

Dec. 20, 2013  (AU) ................ 2013905021

(51) Int. Cl.
*C12N 15/11*     (2006.01)
*C12N 15/113*   (2010.01)
*A01N 57/16*    (2006.01)
*A01N 63/10*    (2020.01)

(52) U.S. Cl.
CPC .......... *C12N 15/1131* (2013.01); *A01N 57/16* (2013.01); *A01N 63/10* (2020.01); *C12N 2310/14* (2013.01)

(58) Field of Classification Search
None
See application file for complete search history.

(56) References Cited

U.S. PATENT DOCUMENTS

| | | |
|---|---|---|
| 2005/0244439 A1 | 11/2005 | Bringley |
| 2009/0108233 A1 | 4/2009 | Lu et al. |
| 2009/0238805 A1 | 9/2009 | Raemaekers et al. |
| 2014/0150134 A1 | 5/2014 | Li et al. |

FOREIGN PATENT DOCUMENTS

| | | |
|---|---|---|
| WO | WO2003/004649 | 1/2003 |
| WO | 2006/045590 | 5/2006 |
| WO | 2012/126276 | 9/2012 |

OTHER PUBLICATIONS

Ghormade et al., Perspectives for nano-biotechnology enabled protection and nutrition of plants, 2011, Biotechnology Advances, vol. 29, pp. 792-803.*
Ladewig et al, Biomaterials 31:1821-1829, 2010 (Year: 2010).*
Bartel, D., (2004) MicroRNAs: Genomics, Biogensis, Mechanism and Function. Cell 116: 281-297.
Baulcombe, D., (2004) RNA silencing in plants. Nature 431: 356-363.
Bin Hussein et al. (2002) Controlled release of a plant growth regulator, alpha-naphthaleneacetate from the lamella of Zn—Al-layered double hydroxide nanocomposite, *Journal of Controlled Release*, 82(2-3), 417-27.
Brosnan, C., N. Mitter, M. Christie, N. Smith, P. Waterhouse & B. Carroll, (2007) Nuclear gene silencing directs reception of long-distance mRNA silencing in *Arabidopsis. Proceedings of the National Academy of Sciences* 104: 14741-14746.
Choy, et al. (2007) Clay minerals and layered double hydroxides for novel biological applications, *Applied Clay Science*, 36 (1-3), 122-132.
Dean et al. (2012) Top 10 fungal pathogens in molecular plant pathology, Molecular Plant Pathology, 13(4), 414-430.
Dietzgen, R. G. & Mitter, N. (2006). Transgenic gene silencing strategies for virus control. Australasian Plant Pathol 35, 605-618.
Duan, H., Richael, C. & Rommens, C. (2012). Overexpression of the wild potato eIF4E-1 variant Eva1 elicits Potato virus Y resistance in plants silenced for native eIF4E-1. Transgenic Res 21, 929-938.
Dubey et al. (2011), Controlled release agrochemicals formulations: A review, *Journal of Scientific and Industrial Research*, 70(2), 105-112.
Gan, D., J. Zhang, H. Jiang, T. Jiang, S. Zhu & B. Cheng, (2010) Bacterially expressed dsRNA protects maize against SCMV infection. *Plant Cell Reports* 29: 1261-1268.
Gardner et al (2001) "Direct synthesis of Aloxide-Intercalated Derivatives of Hydrotalcite-like Layered Double Hydroxides: Precursors for the Formation of Colloidal Layered Double Hydroxide Suspensions and Transparent Thin Films", Adv. Mater., 13(16), 1263-1266.
Gleave, A.P., (1992) A versatile binary vector system with a T-DNA organisational structure conducive to efficient integration of cloned DNA into the plant genome. *Plant Molecular Biology* 20: 1203-1207.
Karthikeyan, A., Deivamani, M., Shobhana, V. G., Sudha, M. & Anandhan, T. (2013). RNA interference: evolutions and applications in plant disease management. Archives of Phytopathology and Plant Protection 46, 1430-1441.

(Continued)

*Primary Examiner* — Elizabeth F McElwain
(74) *Attorney, Agent, or Firm* — Nixon & Vanderhye P.C.

(57) ABSTRACT

Aspects of the present invention relate to a plant-protecting RNAi composition comprising plant-protecting double-stranded RNA adsorbed onto Layered Double Hydroxide (LDH) particles, and to methods for protecting a plant comprising the step of administering to a plant an RNAi composition comprising plant-protecting double-stranded RNA adsorbed onto LDH particles.

17 Claims, 17 Drawing Sheets

Specification includes a Sequence Listing.

(56) References Cited

OTHER PUBLICATIONS

Ladewig et al. (2010) "Controlled preparation of layered double hydroxide nanoparticles and their application as gene delivery vehicles", Applied Clay Science, 1-2, 280-289.
Lecellier, C.H.V., O., (2004) RNA silencing: no mercy for viruses? Immunological Reviews 198: 285-303.
Lilley, C. J., Davies, L. J. & Urwin, P. E. (2012). RNA interference in plant parasitic nematodes: a summary of the current status. Parasitology 139, 630-640.
Mills, S.J., A.G. Christy, J.-M.R. Génin, T. Kameda, & F. Colombo, (2012) Nomenclature of the hydrotalcite supergroup: natural layered double hydroxides. *Mineralogical Magazine* 76: 1289-1336.
Mitter, N. & R.G. Dietzgen, (2012) Use of hairpin RNA constructs for engineering plant virus resistance. *Methods Molcular Biology* 894: 191-208.
Mitter, N., R. Mitchell & R.G. Dietzgen, (2006) Fate of hairpin transcript components during RNA silencing and its suppression in transgenic virus-resistant tobacco. *Journal of Biotechnology* 126: 115-122.
Mitter, N., E. Sulistyowati & R.G. Dietzgen, (2003) Cucumber mosaic virus infection transiently breaks dsRNA-induced transgenic immunity to Potato virus Y in tobacco. *Molecular Plant-Microbe Interactions* 16: 936-944.
Price, D. R. G. & Gatehouse, J. A. (2008). RNAi-mediated crop protection against insects. Trends in Biotechnology 26, 393-400.
Scholthof et al. (2011) Top 10 plant viruses in molecular plant pathology, Molecular Plant Pathology, 12(9), 938-954.
Tenllado, F. & J.R. Diaz-Ruiz, (2001) Double-stranded RNA-mediated interference with plant virus infection. *Journal Virology* 75: 12288-12297.
Tenllado, F., B. Martínez-García, M. Vargas & J.R. Díaz-Ruíz, (2003) Crude extracts of bacterially expressed dsRNA can be used to protect plants against virus infections. *Biomedicalcentral Biotechnology* 3: 3.
Timmons, L. & A. Fire, (2001) Ingestion of bacterially expressed dsRNAs can produce specific and potent genetic interference in *Caenorhabditis elegans. Gene* 263: 103-112.
Tyner, K. M., Schiffman, S. R. & Giannelis, E. P. (2004). Nanobiohybrids as delivery vehicles for camptothecin. Journal of Controlled Release 95, 501-514.
Wong, Y., Markham, K., Xu, Z. P., Chen, M., Lu, G. Q., Bartlett, P. F. & Cooper, H. M. (2010). Efficient delivery of siRNA to cortical neurons using layered double hydroxide nanoparticles. Biomaterials 31, 8770-8779.

Xu ZP and Lu GQ (2006) Layered double hydroxide nanomaterials as potential cellular drug delivery agents, Pure and Applied Chemistry, 78(9), 1771-1779.
International Search Report for PCT/AU2014/000255, dated May 9, 2014, 3 pages.
Written Opinion of the ISA for PCT/AU2014/000255, dated May 9, 2014, 4 pages.
Ghormade et al., "Perspective for nano-biotechnology enabled protection and nutrition of plants", Biotechnology Advances, 2011, vol. 29, No. 6, pp. 792-803.
Ladewig et al., "Efficient siRNA delivery to mammalian cells using layered double hydroxide nanoparticles" Biomaterials, 2010, vol. 31, No. 7, pp. 1821-1829.
Wang et al., "Efficiency of layered double hydroxide nanoparticle mediated delivery of siRNA is determined by nucleotide sequence", Journal of Colloid ad Interface Science, 2012, vol. 369, No. 1, pp. 453-459.
Chen et al., "Reduction of the size of layered hydroxide nanoparticles enhances the efficiency of siRNA delivery", Journal of Colloid and Interface Science, 2013, vol. 390, No. 1, pp. 275-281.
Whyard et al. "Ingested double-stranded RNAs can act as species-specific insecticides" Insect Biochem. Mol. Biol. 39:824-832 (2009).
Zhang et al. "Chitosan/double-stranded RNA nanoparticle-mediated RNA interference to silence chitin synthase genes through larval feeding in the African malaria mosquito (*Anopheles gambiae*)" Insect Mol. Biol. 19:683-693 (2010).
EPO Supplementary European Search Report for related EP 14870784, eleven pages, dated Sep. 29, 2017.
Chen et al., "Transfection and expression of plasmid DNA in plant cells by an arginine-rich intracellular delivery peptide without protoplast preparation," FEBS Letters 581; 1891-1897 (2007).
Contento et al., "Structure and function of endosomes in plant cells," Journal of Cell Science 125; 3511-3518 (2012).
Grand Challenges, "Protect Crops Plants from Biotic Stresses From Field to Market (Round 8)," 1-3; accessed at https://www.grandchallenges.org/challenge/protect-crop-plants-biotic-stresses-field-market-round-8 on May 16, 2019.
Unknown; "QAAFI receives Grand Challenges Exploration Grant for groundbreaking research in global health and development," 1-4 (2012).
Helios Gene Gun System, Life Science Research, 1-2 (2019).
Mitter et al., "Clay nanosheets for topical delivery of RNAi for sustained protection against plant viruses," Nature Plants, vol. 3, Article No. 16207, 1-10 (2017).
Neuhaus et al., "Plant transformation by microinjection techniques," Physiologia Plantarum 79: 213-217 (1990).

\* cited by examiner

SEQUENCE LISTING

<160> NUMBER OF SEQ ID NOS: 8

<210> SEQ ID NO 1
<211> LENGTH: 533
<212> TYPE: DNA
<213> ORGANISM: Artificial Sequence
<220> FEATURE:
<223> OTHER INFORMATION: NIa

<400> SEQUENCE: 1

```
ccatggaggt gcgatctatg cacggtacat tcagggtgaa gaatctacgc agtttgagcg      60
ttctgccaat taaaggtagg gatatcatcc tcatcaaaat gccgaaagat ttccctgtct     120
ttccacagaa attgcatttc cgagctccaa cacagaatga aagagtttgt ttagttggaa     180
ccaactttca ggagaagtat gcatcgtcga tcatcacaga gacaagcacc acttacaata     240
taccgggcag cacattctgg aagcattgga ttgaaacaga taatggacat tgtggactac     300
cagtggtgag taccaccgat ggatgtctag tcggaatcca cagtttggca acaacagac     360 acaccacgaa ctactactca gccttcgatg aagattttga aagcaagtat ctccgaacca     420
atgagcacaa tgaatgggtc aagtcttgga tttataatcc agacacagtg ttgtggggcc     480
cgttgaaact taaagacagc actcccaaag gattattcaa gacaacaaag ctt            533
```

<210> SEQ ID NO 2
<211> LENGTH: 978
<212> TYPE: DNA
<213> ORGANISM: Artificial Sequence
<220> FEATURE:
<223> OTHER INFORMATION: pGEM-IR54 construct

<400> SEQUENCE: 2

```
gtcgactcaa tagcaattac agatagaatc ggtgtacaaa ggtgttaacc ttttcgtcgc      60
agcaccaaaa acaggagatg tttctgacat gcaatattat tacgacaagt gtttgccggg     120
aaacagtact atactcaatg agtatgatgc tgtaactatg caaatacgag agaatagttt     180
gaatgtcaag gattgtgtgt tggatatgtc gaaatcggtg cctcttccga gagaatctga     240
gacgacattg aaacctgtga tcaggactgc tgctgaaaaa cctcgaaaac ctggattgtt     300
ggaaaatttg gtcgcgatga tcaaaagaaa tttcaactct cccgaattag taggggttgt     360
tgacatcgaa gacaccgctt ctctagtagt agataagttt tttgatgcat acttaattaa     420
agaaaagaaa aaaccaaaaa atatacctct gctttcaagg gcgagtttgg aaagatggat     480
cgaaaagcaa gagaagtcaa caattggcca gttggctgat tttgacttta ttgatttacc     540
agccgttgat caatacaggc acatgatcaa gcagcagccg aaacagcgtt tggatcttag     600
tattcaaact gaatacccgg ctttgcaaac tattgtgtat catagcaaga aaatcaatgc     660 gcttttggt cctgtatttt cagaattaac aagacagctg ctagagacaa ttgacagttc     720
aagattcatg ttttatacaa ggaaaacgcc tacacagatc gaagaatttt tctcagatct     780
ggactctaat gttcctatgg acatattaga gctagacatt tccaagtatg acaaatcaca     840
gaacgaattt cattgtgcag tcgagtatga gatttggaaa aggttaggct tagacgattt     900
```

```
cttggctgaa gtttggaaac acgggcatcg aagacaacg ttgaaagact acacagccgg    960
aataaaaacg tgtttgtg                                                 978
```

<210> SEQ ID NO 3
<211> LENGTH: 391
<212> TYPE: DNA
<213> ORGANISM: Artificial Sequence
<220> FEATURE:
<223> OTHER INFORMATION: GFP

<400> SEQUENCE: 3

```
gaattcgatg cccttcagct cgatgcggtt caccagggtg tcgccctcga acttcacctc    60
ggcgcgggtc ttgtagttgc cgtcgtcctt gaagaagatg gtgcgctcct ggacgtagcc   120
ttcgggcatg gcggacttga agaagtcgtg ctgcttcatg tggtcggggt agcggctgaa   180
gcactgcacg ccgtaggtga aggtggtcac gagggtgggc cagggcacgg gcagcttgcc   240
ggtggtgcag atgaacttca gggtcagctt gccgtaggtg gcatcgccct cgccctcgcc   300
ggacacgctg aacttgtggc cgtttacgtc gccgtccagc tcgaccagga tgggcaccac   360
cccggtgaac agctcctcgc ccttgggtac c                                  391
```

<210> SEQ ID NO 4
<211> LENGTH: 18
<212> TYPE: DNA
<213> ORGANISM: Artificial Sequence
<220> FEATURE:
<223> OTHER INFORMATION: SP6

<400> SEQUENCE: 4

```
atttaggtga cactatag                                                 18
```

<210> SEQ ID NO 5
<211> LENGTH: 20
<212> TYPE: DNA
<213> ORGANISM: Artificial Sequence
<220> FEATURE:
<223> OTHER INFORMATION: T7

<400> SEQUENCE: 5

```
taatacgact cactataggg                                               20
```

<210> SEQ ID NO 6
<211> LENGTH: 21
<212> TYPE: DNA
<213> ORGANISM: Artificial Sequence
<220> FEATURE:
<223> OTHER INFORMATION: NIa hairpin DIG

<400> SEQUENCE: 6

```
tcaggagaag tatgcatcgt c                                             21
```

<210> SEQ ID NO 7
<211> LENGTH: 22
<212> TYPE: DNA
<213> ORGANISM: Artificial Sequence
<220> FEATURE:
<223> OTHER INFORMATION: IR54 hairpin DIG

<400> SEQUENCE: 7

```
tgacatcgaa gacaccgctt ct                                            22
```

<210> SEQ ID NO 8

-continued

```
<211> LENGTH: 22
<212> TYPE: DNA
<213> ORGANISM: Artificial Sequence
<220> FEATURE:
<223> OTHER INFORMATION: GF hairpin DIG

<400> SEQUENCE: 8
gaagaagtcg tgctgcttca tg                                  22
```

PLANT-PROTECTING RNAI COMPOSITIONS COMPRISING PLANT-PROTECTING DOUBLE-STRANDED RNA ADSORBED ONTO LAYERED DOUBLE HYDROXIDE PARTICLES

This application is the U.S. national phase of International Application No. PCT/AU2014/000255 filed 14 Mar. 2014, which designated the U.S. and claims priority to AU Patent Application No. 2013905021 filed 20 Dec. 2013, the entire contents of each of which are hereby incorporated by reference.

TECHNICAL FIELD

The present invention relates to, inter alia, plant-protecting compositions, methods for preparing such compositions and to methods for protecting a plant using such compositions.

BACKGROUND ART

It will be clearly understood that, if a prior art publication is referred to herein, this reference does not constitute an admission that the publication forms part of the common general knowledge in the art in Australia or in any other country.

Traditional strategies for the control of plant pests and diseases include techniques such as crop rotation, complementary planting, cross protection, early detection of disease and eradication, breeding for disease resistance and chemical control. Breeding for disease resistance and chemical control are two of the most commonly utilised strategies for the control of plant pests and diseases such as insects, fungi, nematodes and viruses.

Chemical control methods in particular are frequently used to control insects and fungi that affect plants, and also nematodes. However, chemical agents are often expensive, and furthermore there are safety concerns relating to the potential impact of the chemical agent on the environment and the use of chemical agents on, for example, fruits and vegetables to be consumed by people. These last issues are factors that have contributed to the growth of the market for organic fruit and vegetables.

Viruses are more difficult to control, and there are very few, if any, commercially available agents for the treatment of plant viruses. Nevertheless, the impact of plant viruses on crops can be significant. For example, in southeast Asia, infection of rice with Rice tungro virus leads to an estimated annual economic loss of $1.5 billion annually. Furthermore, Tomato spotted wilt virus infects a wide variety of plants including tomato, peanuts and tobacco, leading to estimated annual worldwide losses of about $1 billion.

A natural plant defence mechanism against viruses in plants is RNA interference (RNAi), also known as RNA silencing. There is growing evidence that this mechanism plays an important role in natural plant defences against parasites, viruses, insects, nematodes and fungal infections, as well as transposon activity. Through this mechanism exogenous or endogenous double-stranded RNA (dsRNA) is diced into small interfering RNA (siRNA), which is then incorporated into an RNA-induced silencing complex (RISC). The active RISC then uses the siRNA to detect and degrade targeted viral messenger RNA (mRNA), thereby giving rise to antiviral defence.

Plants may be bred to take advantage of naturally occurring disease resistance to various viruses and other organisms. Alternatively, transgenic plants have been produced which employ RNAi to provide resistance to various viruses. Examples of transgenic plants include the Rainbow™ and Sun Up™ papaya (*Carica* papaya) cultivars which are resistant to the Papaya Ringspot Virus type W. However, there are only a limited number of transgenic RNAi plants commercially available, and large-scale application of transgenic plants has encountered resistance from the public and from regulatory agencies. Furthermore, the cost of developing transgenic plants makes this a laborious and unattractive option.

The RNAi mechanism also may be induced through the exogenous application of dsRNA. However, there has been little research on non-transgenic RNAi approaches to protection of plants. Research that has been performed has illustrated limitations in this approach. For example, in one study topically applied dsRNA could not be detected 7 days post application. Furthermore, when the dsRNA was applied 24 hours after viral infection, the dsRNA was not able to protect the plants (Tenllada and Diaz-Ruiz (2001)). Further studies have illustrated that dsRNA was able to protect *N. benthamiana* when challenged 5 days after spraying, but a delay of 7 days between spray and virus inoculation could not protect the plant from becoming systemically infected (Tenllado et al, (2003) and Gan et al, (2010)). One factor that impacts on the instability of dsRNA in the environment is ultraviolet light which catalyses the breakdown of dsRNA.

Consequently, there is a need to provide an effective alternative approach for the agricultural control of plant viruses, parasites, insects, nematodes or fungal infections, and especially an approach which at least partially overcomes at least one of the abovementioned disadvantages or which provides the consumer with a useful or commercial choice.

SUMMARY OF INVENTION

In a first aspect, the present invention relates to a plant-protecting RNAi composition comprising plant-protecting double-stranded RNA adsorbed onto Layered Double Hydroxide (LDH) particles.

Advantageously, it has been found that such compositions, when applied to plants, are able to provide the plant with protection over an extended period of time against a range of organisms, including plant viruses.

The composition may be for protecting any suitable plant. The plant may be an embryophyte, especially a spermatophyte, more especially an angiosperm (such as a monocotyledon (or monocot), dicotyledon or eudicotyledon (eudicot)) or a gymnosperm.

Exemplary monocots include plants of the order: asparagales (including amaryllidaceae (such as leek, onion, garlic, shallots and chives) and asparagaceac (such as asparagus)); arecales (including arecaceae (such as palms, for example coconut palm)); dioseoreales (including dioscoreaceae (such as yam)); poales (including bromeliaceae (such as pineapple) and poaceae (including corn (maize), wheat, rice, barley, millet, sorghum, oats and bamboo)); and zingiberales (including musaceae (including banana) and zingiberaceae (including ginger and galangal)).

Exemplary eudicots include plants of the order:
Apiales (including apiaceae (such as parsnip, carrot and celery));
Asterales (including asteraceae (such as lettuce, artichoke and sunflower));
Brassicales (including brassicacette (such as broccoli, cabbage, kale, cauliflower, brussel sprouts, bok choy, choi sum, kohlrabi, radish, turnip and rapeseed) and capparaccae (such as capers));

Caryophyllales (including amaranthaceae (such as spinach, chard and beet) and polygonaceae (such as rhubarb));

Cucurbitales (including cucurbitace (such as cucumber, squash, pumpkin, rockmelon, honeydew melon, zucchini and watermelon));

Ericales (including actinidiaceae (such as kiwifruit) and ericaceae (such as blueberry));

Fabales (including fabaceae (such as various beans, pea, soy bean, mung bean, lentil, peanut and alfalfa));

Lamiales (including oleaceae (such as olive));

Malpighiales (including linaceae (such as flax));

Malvales (including malvaceae (such as cotton));

Myrtales (including myrtaceae (such as guava));

Rosales (including cannabaceae (such as hemp), rosaceae (such as strawberry, apple, pear, apricot, plum, cherry, peach, raspberry, alationd, and nectarine) and moraceae (such as fig));

Sapindales (including rutaceae (such as citrus, for example orange, lemon, grapefruit, lime and mandarin) and sapindaceae (such as lychee));

Solanales (including convolvulaceae (such as sweet potato) and solanaceae (such as potato, tomato, eggplant, peppers (such as capsicum) and tobacco)); and Vitales (including vitaceae (such as grape)).

In one embodiment, the composition is for protecting commercial agricultural crops. Exemplify crops include cereals, vegetables (including roots and tubers), fruits, pulses, oilcrops and fibre crops. Cereals may include corn (maize), rice, wheat, barley, sorghum, millet and oats. Vegetables may include broccoli, cauliflower, cabbage, artichokes, capers, kale, spinach, lettuce, bok choy, chard, thoi sum, leeks, brussel sprouts, kohlrabi, galangal, ginger, celery, rhubarb, asparagus, bamboo shoots, potatoes, sweet potatoes, yams, soybeans, mung beans, alfalfa, carrots, parsnips, beets, radishes, turnips, onions, shallots and garlic. Fruits may include tomatoes, grapes, kiwifruit, berrys (including strawberrys, blueberrys and rasberrys), guava, pears, melons (including rockmelons, watermelons and honeydew melons), citrus (including oranges, mandarins, lemons, limes and grapefruits), stonefruit (including apricots, nectarines, plums, cherries and peaches), lychees, pineapples, figs, apples, bananas, cucumbers, squash, zucchinis, pumpkins, peppers, eggplants and avocados. Pulses may include beans, peas and lentils. Oilcrops may include crops from which oil may be obtained, such as palms, soybeans, rapeseeds, sunflower seeds, peanuts, cottonseeds, palm kernels, coconuts and olives. Fibre crops may include cotton, flax, hemp and bamboo. The crop may also be tobacco or a flowering plant.

The plant-protecting double-stranded RNA (dsRNA) may be capable of protecting a plant (especially via RNA interference) against organisms including: a plant virus or viroid, parasite, insect, nematode, fungi or oonivcete; especially against a plant virus or viroid, insect, fungi or oomycete; most especially a plant virus or viroid. Exemplary viruses and viroids include a virus or viroid of the family:

Alphaflexiviridae (especially Potato Virus X (PVX));

Bromoviridae (especially Alfalfa Mosaic Virus (AMV), Cucumber Mosaic Virus, and Brome Mosaic Virus (BMV));

Bunyaviridae (especially Tomato Spotted Wilt virus):

Caulimoviridae (especially Cauliflower Mosaic Virus (CaMV) and Rice Tungro Bacilliform Virus):

Closteroviridae (especially Citrus Tristeza Virus);

Geminiviridae (especially Mungbean Yellow Mosaic India Virus, African Cassava Mosaic Virus. Tomato Yellow Leaf Curl Sardinia Virus. Tomato Yellow Leaf Curl Virus, and African Cassava Mosaic Virus);

Luteoviridae (especially Barley Yellow Dwarf Virus, and Potato Leafroll Virus);

Pospiviroidae (especially Potato Spindle Tuber Viroid);

Potyviridae (especially Potato Virus Y (PVY). Tobacco Etch Virus (TEV), Papaya Ringspot Virus type W (PRSV-W), Plum Pox Virus (PPV), Sugarcane Mosaic Virus, Bean Common Mosaic Virus and Cassava Brown Streak Virus);

Sequiviridae (especially Rice Tungro Spherical Virus);

Tombusviridae (especially Maize Chlorotic Mottle Virus and Tomato Bushy Stunt Virus); and Virgaviridae (especially Tobacco Mosaic Virus (TMV). Tomato Mosaic Virus, Pepper Mild Mottle Virus (PMMoV) and Cucumber Green Mottle Mosaic Virus).

The plant virus may also be a virus of the genus Benyvirus (especially Beet Necrotic Yellow Vein Virus).

Exemplary fungi include *Magnaporthe* species (especially *Magnaporrhe oryzae*), *Botryhs* species especially *Borrytis cinema*), *Puccinia* species, *Fusarium* species (especially *Fusarium graminearum* and *Fusarium oxysporum*), *Blumeria* species (especially *Blumeria graminis f.* sp *Mycosphaerella* species (especially *Mycosphaerella graminicola*), *Colletotrichum* species, *Ustilago* species (especially *Ustilago maydis*), *Melampsora* species (especially *Melampsora lini*), *Phakopsora* species (especially *Phakopsora pachyrhizi*), *Rhizoctonia* species (especially *Rhizoctonia solani*) and *Aspergillus* species.

Exemplary oomycetes include *Phytophthora* species. Exemplary insects include: Cotton bollworm, Corn rootworm, aphids. Diamond Back Moth, Weavils and other lepidopteran insects. An exemplary nematode is root knot nematode. An exemplary parasite is the parasitic weed *Striga asiatica* L.

In one embodiment, the plant-protecting dsRNA is capable of protecting a plant (especially via RNA interference) against a plant virus; especially a plant virus of the family Bromoviridae, Potyviridae or Virgaviridae; most especially a plant virus selected from Cucumber Mosaic Virus Potato Virus Y (PVY) and Pepper Mild Mottle Virus (PMMoV).

A specific dsRNA sequence may be selected based on the organism against which protection is sought, and an appropriate sequence could readily be selected by a skilled person.

Advantageously, in order for RNA interference to occur, the RNA nucleotide sequence must match the organism perfectly. Consequently, the dsRNA is likely to be highly specific to the target organism, limiting the possibility of adverse effects on either the environment or on people at the time of consumption (in the case of vegetables and fruits, for example).

As used herein, the term "plant protecting" and the like means that the composition/dsRNA is able to prevent, treat, or ameliorate the impact of an organism, such as a virus, parasite, insect, nematode or fungi, on a plant. For example, dsRNA which protects a plant against a virus may treat a viral infection, prevent a viral infection from occurring, and/or ameliorate the severity of a viral infection. For the avoidance of doubt, the term "treat" includes both complete and partial treatments (i.e. the plant may still be impacted by the targeted organism after the treatment, but to a lesser extent than prior to the treatment).

The composition may include an effective amount of plant-protecting dsRNA. The term "effective amount"

means that a sufficient quantity of dsRNA is administered so as to treat, prevent, or ameliorate the impact of an organism on a plant.

The length of the dsRNA may vary depending on the organism(s) against which protection is sought. Advantageously, RNases in plants (Dicer-Like enzymes) will cleave long dsRNA sequences into much smaller fragments, each of which is typically 21-25 nucleotides in length. Therefore, long dsRNA sequences of, for example, 100 to 3000 base pairs may be used, and these longer sequences would be cleaved into such smaller fragments by the plant as the dsRNA is released from the LDH. It is believed that these smaller 21 nucleotide fragments are involved in the RNA interference mechanism.

A single dsRNA construct may be engineered by combining specific sequences from multiple pathogens and pests which could target multiple organisms, as the plant will cleave the dsRNA sequence into shorter fragments. For example, a single dsRNA construct could be used to target three different viruses and two different insects. The dsRNA may target at least two organisms, more especially from 2 to 10 organisms, even more especially from 4 to 8 organisms.

The dsRNA may therefore be from 21 to 3000 base pairs in length especially from 21 to 2500, or from 21 to 2000 base pairs in length; more especially from 80 to 1750, from 80 to 1500, or from 80 to 1200 base pairs in length; most especially from 100 to 1200, from 250 to 1200, from 300 to 1200 or from 400 to 1000 base pairs in length. Advantageously, use of such longer dsRNA sequences provides a much greater likelihood of the sequence being cleaved to a nucleotide sequence that will match with the desired organism to affect (e.g. kill) the organism. Also, it is significantly less expensive to produce one longer dsRNA construct that will target multiple organisms, rather than multiple short dsRNA sequences which each target one organism.

It has surprisingly been found that LDH is able to bind to dsRNA sequences of a variety of lengths regardless of the sequence.

In one embodiment, the dsRNA is Nuclease Inclusion a (NIa) against Potato Virus Y, or a pGEM-IR54 construct against Pepper Mild Mottle Virus.

In another embodiment, the dsRNA includes a strand (antisense or sense) which is complementary to or at least partly complementary to a sequence as set forth in SEQ ID NOs. 1, 2 or 3; more especially SEQ ID NOs. 1 or 2. As used herein, the phrase "at least partly complementary" means that one strand of the dsRNA has at least 50%, at least 55%, at least 60%, at least 65%, at least 70%, at least 75%, at least 80%, at least 85%, at least 90%, or at least 91%, 92%, 93%, 94%, 95%, 96%, 97%, 98% or 99% sequence identity with the sequence. It would be appreciated that this definition takes into account that RNA uses a U instead of a T, as found in DNA.

In a further embodiment, the dsRNA includes a strand (antisense or sense) which is complementary to or at least partly complementary to a fragment of a sequence as set forth in SEQ ID NOs. 1, 2 or 3; more especially SEQ ID NOs. 1 or 2. By way of example only, a fragment may include at least 5%, 10%, 15%, 20%, 25%, 30%, 35%, 40%, 45%, 50%, 55%. 60%, 65%, 70%, 75%, 80%, 85%, 90% or 95% of a sequence which is complementary to or at least partly complementary to a sequence as set forth in SEQ ID NOs. 1, 2 or 3; more especially SEQ ID NOs. 1 or 2.

The dsRNA may be produced in any suitable way. For example, the dsRNA may be produced in vitro via a kit, in vitro or in vivo via a bacteriophage (such as via a *Pseudomonas syringae* dsRNA bacteriophage), or in vivo using a specialised strain of organism, especially using a bacteria (such as a strain of *E. coli*). Typically, in vitro methods are suitable for smaller scale dsRNA production. For large scale production, in vivo production methods are preferred. The dsRNA used may be a crude bacterial extract.

The dsRNA may be in any suitable form and be of any suitable sequence. The dsRNA may include any suitable modifications. For example, the dsRNA may include one or more modified phosphate groups, modified nucleic acids/nucleotides, modified sugars and/or modified 5 or 3 prime ends, Exemplary modified groups which may be present in the dsRNA include, for example, inosine, methylinosine, pseudouridine, morpholine, locked nucleic acids, peptides (such as peptide nucleic acids (PNA)), biotin, cholesterol, fluorophores, radionuclides and metals. The dsRNA may also be in the form of a dsRNA construct. Such modifications may enhance the stability and/or longevity of the dsRNA.

The dsRNA is typically anionic, and interacts with (and is especially intercalated between) cationic LDH layers, A diagram illustrating a loading and release of dsRNA onto and from LDH is provided in FIG. 1.

LDHs (layered double hydroxides) are mixed hydroxides of divalent and trivalent metals having an excess of positive charge that is balanced by interlayer anions. Common forms of LDH comprise $Mg^{2+}$ and $Al^{3+}$ (known as hydrotalcites) and $Mg^{2+}$ and $Fe^{3+}$ (known as pyroaurites) but LDHs containing other cations including Ni, Zn, Mn, Ca, Cr, and La are known. The amount of surface positive charge generated is dependent upon the mole ratio of the metal ions in the lattice structure, and the conditions of preparation as they affect crystal formation.

The LDH may have the general formula (1):

$$M^{II}_{1-x}M^{III}_{x}(OH)_2 A^{n-}_{x/n} \cdot yH_2O \qquad (1)$$

where $M^{II}$ and $M^{III}$ are di- and tri-valent metal ions respectively and $A^n$ is the interlayer anion of valance n. The x value represents the proportion of trivalent metal to the total amount of metal ion present and y denotes variable amounts of interlayer water. A limited portion of $A^{n-}$ may be present on the LDH particle surface (for example, 5-40%, more especially 8-30% most especially 10-20%). This may explain why some dsRNA is adsorbed on the surface.

General formula (I) may also be written as formula (2):

$$M^{II}_n M^{III}(OH)_{2(n+1)} X \cdot yH_2O \qquad (2)$$

wherein X is one or more anions or negatively charged material to balance charge in the hydroxide layer. X is typically present in the interlayer space in the LDH material. A limited portion of X may be present on the LDH particle surface (for example, 5-40%, more especially 8-30% most especially 10-20%). This may explain why some dsRNA is adsorbed on the surface.

$M^{II}$ is suitably Mg, although other metal ions of valence 2+ may also be used. $M^{III}$ is suitably Al. It will be appreciated that other metal ions of valence 3+ may also be used. Examples of other metal ions that may be used include:

$M^{II}$: Fe, Co, Ni, Cu, Zn, Mn, Pd. Ti, Cd and Ca $M^{III}$: Co, Fe, Mn, Ga, Rh, Ru, Cr, V, In, Y, Gd, Ni and La.

These lists should not be considered to be limiting.

Exemplary anions in formulae (1) or (2) (i.e. $A^{n-}$ or X) include, but are not limited to, $(CO_3)^{2-}$, $(SO_4)^{2-}$, Cl, OH, $S^{2-}$ and $[Sb(OH)_6]^-$.

The LDH may include a general layer of formula (3)

$$[M^{II}_{1-x}M^{III}_x(OH)_2]^{x+} \qquad (3)$$

where $M^{II}$, $M^{III}$ and x are as defined above for formulae (1) and (2), and the positive charge x+ is balanced by anions (as may be described above for formulae (1) and (2)) which are intercalated between the layers.

The LDH may be of the hydrotalcite group, the quintinite group, the fougèrite group, the woodwardite group, the cualstibite group, the glaucocerinite group, the wermlandite group, and the hydrocalumite group; especially of the hydrotalcite group; more especially hydrotalcite ($Mg_6Al_2(OH)_{16}CO_3\_4H_2O$). The hydrotalcite group is LDH of general formula (1), (2) or (3) in which $M^{II}:M^{III}$ is 3:1 (especially in which $M^{II}$ is Mg and $M^{III}$ is Al) with a layer spacing of 6.8 to 8.8 Å, especially of 7.3 to 8.3 Å, more especially of 7.6 to 8.0 Å, most especially about 7.8 Å. A discussion on the hydrotalcite group, the quintinite group, the fougèrite group, the woodwardite group, the cualstibite group, the glaucocerinite group, the wermlandite group, and the hydrocalumite group may be found in Mills et al., 2012. In another embodiment, the LDH is of general formula (1), (2) or (3) in which $M^{II}$ is Mg and $M^{III}$ is Al.

Exemplary LDH, and methods of making LDH, are described in Australian Patent No. 2005318862, the contents of which are incorporated herein by reference. Advantageously, in the method described in this patent the size of the LDH can be precisely controlled, and the hydrothermal treatment can disperse the LDH agglomerates into individual LDH nanoparticles.

The LDH particles may have a largest dimension within the range of up to 5 μm, more especially up to 1 μm, most especially up to 750 nm or up to 500 nm. In one embodiment, the LDH particles may have a largest dimension within the range 20-400 nm, more suitably 40-300 nm or 50-200 nm, even more suitably about 120 nm, with the thickness of the particles predominantly falling within the range of 5-40 nm, especially 15-20 nm. The particles may also exhibit a narrow particle size distribution, and the particles may show a particle size distribution of ±20% around the average size. The LDH particles may have an aspect ratio that falls within the range of from 5 to 10 (the 'aspect ratio' relates to the ratio of the largest dimension of the particle to its thickness or height). The LDH particles may combine together to form an average layer of 20-25 positively charged sheets.

In one embodiment, the dsRNA adsorbed onto the LDH has one or more of the dimensions, particle size distribution, or aspect ratio listed above for LDH particles. Scanning Electron Microscope images have confirmed that the morphology of the LDH particles is kept unchanged after loading dsRNA, as a result of the adsorption of dsRNA.

The RNAi composition may be in any suitable form. For example, the RNAi composition may be in the form of a solid, ointment, gel, cream, powder, paste, suspension, colloid, foam or aerosol; especially a suspension or a colloid. Solid forms of the composition may include dusts, powders, granules, pellets, pills, pastilles, tablets, filled films (including seed coatings) and the like, which may be water-dispersible ("wettable"). In one embodiment, the composition is in the form of a concentrate, especially a concentrate in the form of a colloid or suspension.

In one embodiment the composition is heterogeneous, especially comprising a solid phase dispersed within a fluid phase. The solid phase may comprise the plant-protecting double-stranded RNA adsorbed onto LDH particles. The fluid phase may be, for example, a liquid, a gas, or a free flowing solid, or a combination thereof; especially a liquid: more especially an aqueous liquid; most especially water. The water may be sterile or non-sterile. The solid-phase may be dispersed within the fluid phase in any suitable way. This will depend upon the nature of the solid-phase and the fluid-phase.

Depending on the form of the composition, the composition may include a variety of other agents. Exemplary agents include, but are not limited to, one or more of the following types of ingredients: diluents, carriers, excipients, suspension agents, agglomeration agents, bases, buffers, bittering agents, fragrances, preservatives, propellants, thixotropic agents, anti-freezing agents, and colouring agents. Suitable agents may be selected by a skilled person.

The composition may also include one or more other active ingredients. An active ingredient, as defined herein, is an ingredient that provides benefit to a plant. The active ingredient may be, for example, an insecticide, a pesticide, a fungicide, an antibiotic, an insect repellant, an anti-parasitic agent, an anti-viral agent, or a nematicide.

When the composition is in the form of a colloid or suspension, it may include dsRNA-LDH particles at 10% w/w, especially up to 5% w/w or up to 2% w/w, even more especially about 1% w/w, most especially less than 1% w/w.

In another embodiment, when the composition is in the form of a colloid or suspension, it may include dsRNA-LDH particles at up to 100 mg/L; especially up to 50 mg/L; more especially up to 20 mg/L or up to 10 mg/L; most especially less than 10 mg/L. In one embodiment, the concentration of dsRNA-LDH in a colloid or suspension is from 1-100 mg/L.

The composition may be formulated for administration to the plant, or to any part of the plant, in any suitable way. For example, the composition may be formulated for administration to the leaves, stein, roots, fruit, vegetables, grains and/or pulses of the plant. In one embodiment, the composition is formulated for administration to the leaves of the plant, and is especially sprayable onto the leaves of the plant. The composition may be administered to the plant as a metered dose. The composition may be formulated for administration to the plant, for example, by spraying, by brush or by another applicator.

The composition may be in the form of a suspension, in which case the composition may be sprayable onto the plant. The suspension may be substantially stable. As used herein, a "substantially stable" suspension is a suspension in which, once formed, the solid phase remains sufficiently dispersed (i.e. does not significantly aggregate) in the fluid phase (especially a liquid phase, more especially water) for the suspension to be sprayed onto a plant. In one embodiment, the solid phase remains dispersed in the fluid phase for at least 24 hours after the suspension is formed, especially at least 5 days after the suspension is formed, more especially at least 10, 15, 20 or 30 days after the suspension is formed, most especially at least 60 days after the suspension is formed. If the suspension is not substantially stable, then the solid phase may aggregate leading to blockages in equipment when the suspension is sprayed onto plants, or alternatively leading to variable amounts of solid phase material being applied in a given area, resulting in incomplete protection for plants.

Without wishing to be bound by theory, it is believed that the dsRNA adsorbs onto the LDH via anion exchange between the dsRNA and the anions in the LDH (such that cationic portions of the LDH interact with the anionic phosphate groups of the dsRNA). It is believed that when dsRNA is adsorbed onto LDH, the dsRNA is afforded some protection against RNases and U.V. light, and thus the dsRNA is significantly more stable. Thus, it is believed that the LDH acts as a protective coating for the adsorbed dsRNA.

Advantageously, it has been found that when dsRNA is adsorbed onto LDH, the dsRNA substantially does not degrade, even when stored for 60 days. When the dsRNA is adsorbed onto LDH, the LDH advantageously protects the dsRNA against RNase and UV light.

The dsRNA may be adsorbed onto the LDH by any suitable method. Advantageously, one method of adsorbing the dsRNA onto the LDH simply involves incubating the dsRNA with the LDH in an aqueous solution with shaking (for example, at from 100 to 300 rpm, especially at 200 rpm), and at a temperature from 20 to 50° C., especially from 25 to 45° C., or from 30 to 45° C., most especially about 37° C.

The dsRNA may also be adsorbed onto the LDH at any suitable loading ratio. Exemplary loading ratios (by mass) include from 2:1 to 1:20 dsRNA:LDH or from 1:1 to 1:10 dsRNA:LDH: more especially from 1:1 to 1:6 dsRNA:LDH or from 1:1 to 1:5 dsRNA:LDH; most especially from 1:1 to 1:4 dsRNA:LDH, from 1:1 to 1:2.5 dsRNA:LDH, from 1:2 to 1:5 dsRNA:LDH or from 1:3 to 1:4 dsRNA:LDH. The loading ratio may be 1:1, 1:1.5, 1:2, 1:2.5, 1:3, 1:3.5 or 1:4 dsRNA:LDH.

As used herein, the term "adsorbed" includes both circumstances in which dsRNA is adsorbed onto the surface of an LDH layer, as well as circumstances in which dsRNA is intercalated between LDH layers (which would inherently also involve some adsorption).

It may be advantageous when preparing the composition to use more dsRNA than can be adsorbed on the LDH. This is because if the dsRNA is completely adsorbed on the LDH, then dsRNA may not be immediately available on the plant; some of the LDH would need to break down, or some anion exchange must occur (for example via capture of $CO^2$ and conversion to $HCO_3^-/CO_3^{2-}$ for anion exchange), before any dsRNA becomes available. Therefore, by using more dsRNA in the composition than can be adsorbed on the LDH, the composition can provide immediate protection to the plant after application. In one embodiment, from 50% to 95% of the dsRNA in the composition is adsorbed onto the LDH (allowing the remainder to be available as free dsRNA); especially from 60% to 90% of the dsRNA in the composition is adsorbed onto the LDH; most especially from 70% to 80% of the dsRNA in the composition is adsorbed onto the LDH. As a rough estimate, at a dsRNA:LDH mass ratio of 1:10, most dsRNA is adsorbed on the LDH surface, At a dsRNA:LDH mass ratio of 1:5, approximately 50% is adsorbed onto the LDH surface, approximately 30-40% is intercalated, and 10-20% is free in solution.

Advantageously, the composition may be adapted to provide controlled release of the dsRNA after it has been administered to a plant. Without wishing to be bound by theory, after dsRNA:LDH particles are administered to the plant, the particles may functionally remain as a stable surface coating. As the particles interact with moisture and $CO_2$ from the plant and/or the environment, the moisture and $CO_2$ simultaneously hydrate and activate the LDH. The LDH slowly releases dsRNA through reverse anion exchange and/or degradation of the LDH framework. The dsRNA will therefore be protected from degradation and provide the plant with protection against the targeted organism for a longer time period than would be provided using "naked" dsRNA sprays. Furthermore, moisture and $CO^2$ entering the system that might cause pathogen activation will simultaneously hydrate and activate the LDH particles, providing protection to the plant when it is most needed.

The dsRNA may be released from the LDH at an acidic pH, especially at a pH of below 6 or below 5, more especially at a pH of below 4 or below 3, most especially at a pH of below 2. Advantageously, it is believed that atmospheric $CO_2$ will convert to carbonic acid, reducing the pH and allowing slow release of the dsRNA through reverse anion exchange and/or degradation of the LDH framework.

Advantageously, in some embodiments of the present invention the LDH is able to break down into biocompatible components (such as $Mg^{2+}$, $Al(OH)_3$ and $NO_3^-$). Furthermore, even if there is some LDH remaining on, for example, a vegetable at the time of consumption, it may be biocompatible. For example, a LDH such as hydrotalcite (e.g. $Mg_6Al_2(OH)_{16}CO_3.4H_2O$) is a widely used commercial anti-ulcer drug. Hydrotalcite is not toxic to most mammalian cells at concentrations up to 200 μg/ml, and does not lead to any side effect when injected intravenously into rats at 200 mg hydrotalcite/kg. Thus the toxicity to plant cells and leaf cells by the LDH may be limited.

In one embodiment, the composition once administered to a plant, is capable of protecting the plant for at least 15 days, especially at least 20 days, more especially at least 25 days, most especially at least 30 days. In a further embodiment, the composition, once administered to a plant, is capable of protecting the plant for from 2 to 8 weeks, especially from 3 to 6 weeks, most especially from 4 to 5 weeks. Once administered to a plant, the LDH nanoparticles may degrade at a rate of 10-30% per week, especially 15-25% per week, more especially at a rate of 15-20% per week. The duration of protection may be affected, for example, by the amount of rainfall on the plant. Therefore, in a drier climate it is expected that the duration of protection would be increased, whereas a shorter duration of protection may be provided in a wetter climate.

In one embodiment, when the dsRNA:LDH is administered to a plant it is able to provide a from 2 to 10 fold increase in the duration of protection to the plant (especially from 4 to 8 fold, more especially from 5 to 7 fold, most especially at least 6 fold) over the use of the dsRNA alone.

In a second aspect, the present invention relates to a method for protecting a plant, the method comprising the step of administering to a plant an RNAi composition comprising plant-protecting double-stranded RNA adsorbed onto LDH particles.

Features of the second aspect of the present invent ion may be as described for the first aspect. In one embodiment, for example, the step of administering to a plant an RNAi composition comprises spraying the RNAi composition onto the leaves of the plant.

The composition may also be administered to the plant at any suitable concentration, and advantageously the dsRNA in the composition may be effective at relatively low concentrations. In one embodiment, less than 100 μg of dsRNA per plant may be administered, especially less than 50 μg, more especially less than 40, 30, 20, 10 or 5 μg, most especially less than 1 μg or 0.5 μg of dsRNA per plant. When the composition is administered to the leaf of the plant, less than 100 μg of dsRNA per leaf may be administered to the plant, especially less than 50 μg, more especially less than 40, 30, 20, 10 or 5 μg, most especially less than 1 μg or 0.5 μg of dsRNA per leaf is administered to the plant.

In a third aspect, the present invention provides the composition of the first aspect, when applied to a plant.

In a fourth aspect, the present invention provides a method for preparing a plant protecting RNAi composition, comprising the step of adsorbing plant-protecting double-stranded RNA onto LDH particles. In one embodiment, the composition is in the form of a colloid or suspension. In this embodiment, the dsRNA may be adsorbed onto the LDH particles in an aqueous solution. The resultant colloid/suspension may be substantially stable and sprayable onto the plant.

In a fifth aspect, the present invention provides plant-protecting double-stranded RNA adsorbed onto LDH particles.

In a sixth aspect, the present invention provides a kit comprising:
(i) LDH particles; and
(ii) Plant-protecting double-stranded RNA:
wherein the plant-protecting double-stranded RNA is absorbable onto the LDH particles.

In one embodiment of this aspect, the LDH particles and/or the plant-protecting double-stranded RNA is provided in solid or liquid (especially aqueous) form. The LDH particles and/or the plant protecting dsRNA may, depending on their form, include a variety of other agents. Exemplary agents include, but are not limited to, one or more of the following types of ingredients: diluents, carriers, excipients, suspension agents, agglomeration agents, bases, buffers, bittering agents, fragrances, preservatives, propellants, thixotropic agents, anti-freezing agents, and colouring agents. Suitable agents may be selected by a skilled person.

The kit may also include one or more other active ingredients. An active ingredient, as defined herein, is an ingredient that provides benefit to a plant. The active ingredient may be, for example, an insecticide, a pesticide, a fungicide, an antibiotic, an insect repellant, an anti-paracitic agent, an anti-viral agent, or a nematicide.

Features of the third to sixth aspects of the present invention may be as described above for the first and second aspects.

Any of the features described herein can be combined in any combination with any one or more of the other features described herein within the scope of the invention.

BRIEF DESCRIPTION OF DRAWINGS

Various embodiments of the invention will be described with reference to the following drawings, in which.

Figure 1:
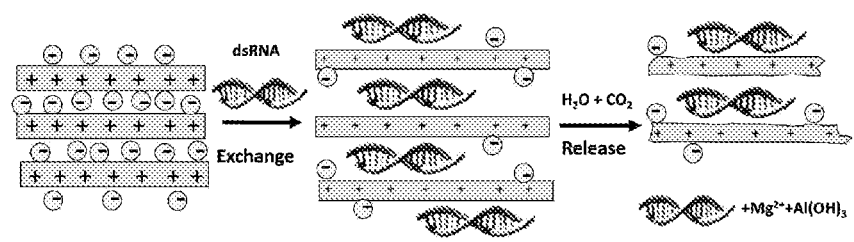
FIG. 1 is a diagram illustrating the loading and release of dsRNA onto LDH.

Preferred features, embodiments and variations of the invention may be discerned from the following Examples which provides sufficient information for those skilled in the art to perform the invention. The following Examples are not to be regarded as limiting the scope of the preceding Summary of the Invention in any way.

EXAMPLES

Targets used for topical application of dsRNA
The targets used were:
Potato Virus Y (PVY)—The Nuclease Inclusion a (NIa) hairpin was previously designed and tested by the Mitter Laboratory (The University of Queensland) (Mitter et al., 2003, Mitter et al., 2006, Mitter & Dietzgen, 2012) and consists of a 446 bp Tobacco peroxidase intron flanked by 735 bp fragments of sense and antisense PVY gene NIa cloned in the binary vector pART7 (Gleave, 1992) that does not encode the required T7 promoter elements for the expression of an RNA hairpin. The partial NIa sequence used for the expressing the dsRNA was 533 bp. This sequence is provided below and in SEQ ID NO: 1.

CCATGGAGGTGCGATCTATGCACGGTACATTCAGGGTGAAGAATCTACGC

AGTTTGAGCGTTCTGCCAATTAAAGGTAGGGATATCATCCTCATCAAAAT

GCCGAAAGATTTCCCTGTCTTTCCACAGAAATTGCATTTCCGAGCTCCAA

CACAGAATGAAAGAGTTTGTTTAGTTGGAACCAACTTTCAGGAGAAGTAT

GCATCGTCGATCATCACAGAGACAAGCACCACTTACAATATACCGGGCAG

CACATTCTGGAAGCATTGGATTGAAACAGATAATGGACATTGTGGACTAC

CAGTGGTGAGTACCACCGATGGATGTCTACTTCCTGAATCCACAGTTTGG

CAAACAACAGACACACCACGAACTACTACTCAGCCTTCGATGAAGATTTT

GAAAGCAAGTATCTCCGAACCAATGAGCACAATGAATGGGTCAAGTCTTG

GATTTATAATCCAGACACAGTGTTGTGGGCCCGTTGAAACTTAAAGACA

GCACTCCCAAAGGATTATTCAAGACAACAAAGCTT

Pepper Mild Mottle Virus (PMMoV)—The pGEM-IR54 construct in the bacterial strain HT115 (DE3) was a kind gift from F. Tentlado, Centro de Inestigaciones Biológicas, Madrid, Spain. The IR54 RNA hairpin targets a 997 bp region of the PMMoV replicase gene (Tenllado et al., 2003). The sequence used for expressing the dsRNA is provided below and in SEQ ID NO: 2.

GTCGACTCAATAGCAATTACAGATAGAATCGGTGTACAAAGGTGTTAACC

TTTTCGTCGCAGCACCAAAAACAGGAGATGTTTCTGACATGCAATATTAT

TACGACAAGTGTTTGCCGGGAAACAGTACTATACTCAATGAGTATGATGC

TGTAACTATGCAAATACGAGAGAATACTTTTGAATGTCAAGGATTGTGTG

TTGGATATGTCGAAATCGGTGCCTCTTCCGAGAGAATCTGAGACGACATT

GAAACCTGTGATCAGGACTGCTGCTGAAAAACCTCGAAAACCTGGATTGT

TGGAAAATTTGGTCGCGATGATCAAAAGAAATTTTCAACTCTCCCGAATT

AGTAGGGGTTGTTGACATCGAAGACACCGCTTCTCTAGTAGTAGATAAGT

TTTTTGATGCATACTTAATTAAAGAAAAGAAAAAACCAAAAAATATACCT

CTGCTTTCAAGGGCGAGTTTGGAAAGATGGATCGAAAAGCAAGAGAAGTC

AACAATTGGCCAGTTGGCTGATTTTGACTTTATTGATTTACCAGCCGTTG

ATCAATACAGGCACATGATCAAGCAGCAGCCGAAACAGCGTTTGGATCTT

AGTATTCAAACTGAATACCCGGCTTTGCAAACTATTGTGTATCATAGCAA

GAAAATCAATGCGCTTTTTGGTCCTGTATTTTCAGAATTAACAAGACAGC

TGCTAGAGACAATTGACAGTTCAAGATTCATGTTTTATACAAGGAAAACG

CCTACACAGATCGAAGAATTTTTCTCAGATCTGGACTCTAATGTTCCTAT

GGACATATTAGAGCTAGACATTTCCAAGTATGACAAATCACAGAACGAAT

TTCATTGTGCAGTCGAGTATGAGATTTGGAAAAGGTTAGGCTTAGACGAT

TTCTTGGCTGAAGTTTGGAAACACGGGCATCGGAAGACAACGTTGAAAGA

CTACACAGCCGGAATAAAACGTGTTTGTG

Green Florescent Protein (GFP)—The GF hairpin was previously designed and tested by the Carroll Laboratory (The University of Queensland) in the pUQC251 construct (Brosnan et al., 2007). The GF hairpin consists of two 391 bp GF fragments that target the 5' end of GFP (S65T) mRNA flanking an intron-splicible inverted repeat spacer (793 bp). The sequence used for expressing the dsRNA is provided below and in SEQ ID NO: 3.

GAATTCGATGCCCTTCAGCTCGATGCGGTTCACCAGGGTGTCGCCCTCGA

ACTTCACCTCGGCGCGGGTCTTGTAGTTGCCGTCGTCCTTGAAGAAGATG

GTGCGCTCCTGGACGTAGCCTTCGGGCATGGCGGACTTGAAGAAGTCGTG

CTGCTTCATGTGGTCGGGGTAGCGGCTGAAGCACTGCACGCCGTAGGTGA

AGGTGGTCACGAGGGTGGGCCAGGGCACGGGCAGCTTGCCGGTGGTGCAG

ATGAACTTCAGGGTCAGCTTGCCGTAGGTGGCATCGCCCTCGCCCTCGCC

GGACACGCTGAACTTGTGGCCGTTTACGTCGCCGTCCAGCTCGACCAGGA

TGGGCACCACCCCGGTGAACAGCTCCTCGCCCTTGGGTACC

Control—MEGAseript® RNAi kit control (500 bp).

Example 1

Construction and Expression of dsRNA Vectors

Construction of dsRNA Expression Vectors

NIa hairpin was subcloned by Nco I restriction endonuclease digestion into the pGEM®-T Vector System 1 (Promega, Madison, Wis., U.S.A) using E. coli strain JM109 as per manufacturer's protocol, generating pGEM-NIa hairpin. pGEM-NIa hairpin was sequenced with standard SP6 and T7 printers (Table 1), at 9.6 pM with 500-600 nM pGEM-NIa hairpin and made to a final volume of 12 µl, with diethyl pyrocarbonate (DEPC) treated water. Samples were sent to the Australian Genome Research Facility (Brisbane, Australia) for capillary separation sequencing. The Nco I excised NIa hairpin fragment was also subcloned into the vector L4440 as above, generating the construct L4440-NIa hairpin. L4440-NIa hairpin vector was maintained and propagated in the E. coli strain Top10 (One Shot® TOP10 Electrocomp™ E. coli, (Life Technologies, Carlsbad, Mass., U.S.A.)). GF hairpin was subcloned by Eco RI restriction endonuclease digestion as above, except maintained in One Shot® TOP10 Electrocomp E. coli as per the instruction manual instead of JM109. Restriction profiles of all plasmids were resolved in a 1% agarose gel. All gels in this example were resolved with 0.1% ethidium bromide 10 mg/mL, 40 mM Tris/20 mM acetic acid/1 mM ethylenediaminetetraacetic acid (EDTA) (1×TAE) at 60V for 1 hour.

NIa and IR54 Hairpin dsRNA Expression Vectors

Figure 2:
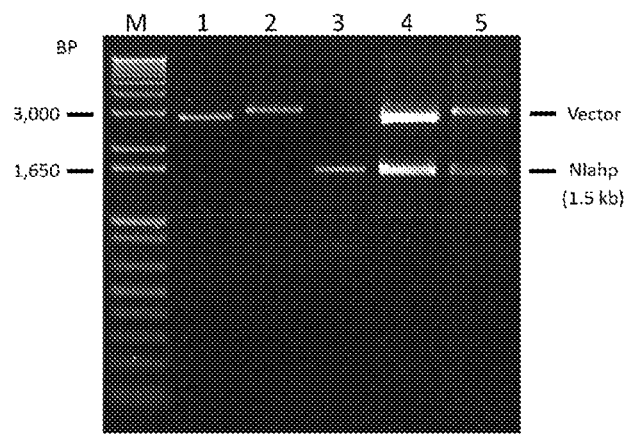
FIG. 2 is a gel electrophoresis restriction profile of NIa hairpin constructs.

The NIa hairpin sequence under the expression of a T7 promoter(s) was constructed by restriction endonuclease digestion and ligation to generate pGEM-NIa hairpin and L4440-NIa hairpin expression vectors. The resulting constructs showed the correct restriction digestion profile with Nco I of 3,000 bp pGEM-T or 2,800 bp L4440 vector and 1,512 hp of NIa hairpin (FIG. 2). In FIG. 2 Lane 1 is Nco I digested L4440 (2,800 bp); Lane 2 is Arco I digested pGEM-T (3,000 bp); Lane 3 is Nco I digested and gel extracted NIa hairpin (1,512 bp); Lane 4 is Nco I digested L4440-NIa hairpin; Lane 5 is Nco I digested pGEM-NIa hairpin: and M is 1 kb+ ladder. Sequencing and BLAST analysis confirmed the NIa sequence was correct in pGEM-NIa hairpin, which was used to create L4440-NIa hairpin.

IR54 was kindly sent as pGEM-IR54 hairpin by F. Tenllado, requiring no alterations to the PMMoV targeted vector.

GF Hairpin dsRNA Expression Vector

Figure 3:
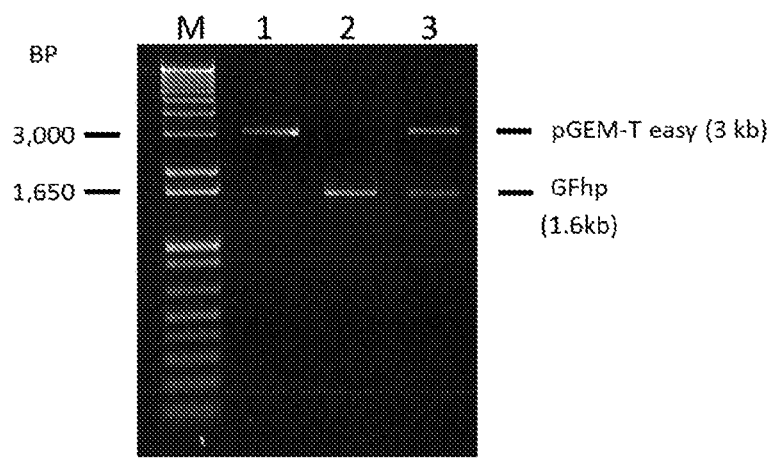
FIG. 3 is a gel electrophoresis restriction digestion profile of pGEM-GF hairpin construct.

The GE hairpin was cloned into pGEM-T easy through ligation of restriction enzyme processed pUQC251 and pGEM-T easy. The resulting pGEM-GF hairpin plasmid showed the expected restriction profile of 3,000 bp pGEM-T easy and 1,575 bp GF hairpin when digested with Eco RI (FIG. 3). In FIG. 3, Lane 1 is Eco RI digested pGEM-T easy (1,575 bp): Lane 2 is Eco RI digested and gel extracted GF hairpin (1,575 bp); Lane 3 is Eco RI digests of plasmids pGEM-GF hairpin; and M is 1 kb+ ladder.

In Vitro and In Vivo Transcription of dsRNA Expression Vectors

In vitro transcription: The pGEM-NIa, L4440-NIa, pGEM-IR54 and pGEM-GF hairpin plasmids were linearised with Pvu I and phenol:chloroform:isoamyl alcohol purified for in vitro transcription using the MEGAscript® RNAi kit (Life Technologies, Carlsbad, Mass., U.S.A.) as per manufacturer's protocol.

In vivo transcription: Plasmids were transformed into the *E. coli* strain HT115 (DE3) (*Caenorhabditis* Genetics Center, Minn., U.S.A.). $CaCl_2$ chemical competency of HT115 cells, transformation and induction protocols used were supplied with the bacteria (Timmons & Fire, 2001). Total RNA was extracted with TRIzol® Reagent (Life Technologies, Carlsbad, Mass. U.S.A.) as per manufacturer's protocol and treated with DNase I and RNase A under high salt conditions (0.3 M NaCl 0.030 M sodium citrate). The average yield of dsRNA obtained from HT115 was 0.5 mg/mL from a starter culture of 100 mL.

Production of NM and IR54 dsRNA

Figure 4:
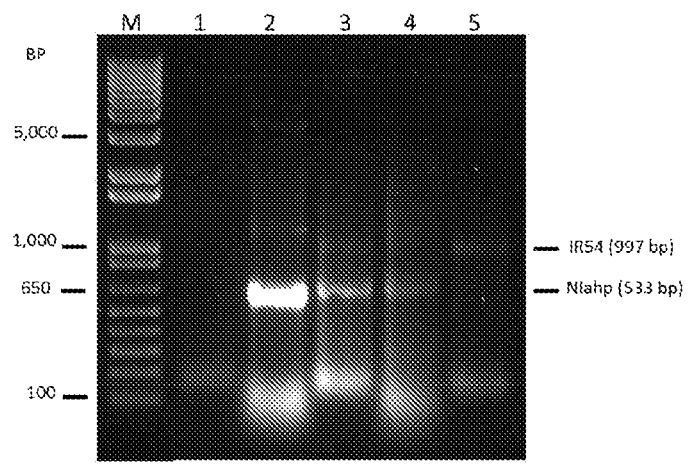
FIG. 4 is an agarose gel electrophoresis of in vitro and in vivo expressed NIa and IR54 dsRNA.

The pGEM-NIa and L4440-NIa hairpins were used for in vitro or in vivo expression requiring transformation into the tetracycline resistant *E. coli* strain HT115 (DES). The resultant in vitro or in vivo derived dsRNA was resolved by agarose gel electrophoresis (FIG. 4). In FIG. 4, Lane 1 is HT115 expressed pGEM-NIa hairpin (1 µL); Lane 2 is in vitro expressed pGEM-NIa hairpin (0.5 µL); Lane 3 is HT115 expressed L4440-NIa hairpin (1 µL), Lane 4 is in vitro expressed L4440-NIa hairpin (0.5 µL); Lane 5 is HT115 expressed pGEM-IR54 hairpin (1 µL); and M is 1 kb+ ladder. Higher yields per µL were obtained for in vitro transcribed pGEM-NIa hairpin and L4440-NIa, hairpin (Lanes 2 and 4), however, the kit only produces 150 µL dsRNA per reaction. HT115 expressed dsRNA from pGEM-NIa hairpin did not appear to express the NIa dsRNA (Lane 1), L4440-NIa hairpin expressed in HT115 (Lane 3) yielded a volume of 1 mL at an approximate 1:2 dilution of in vitro transcribed (Lane 4).

Production of GF dsRNA

Figure 5:
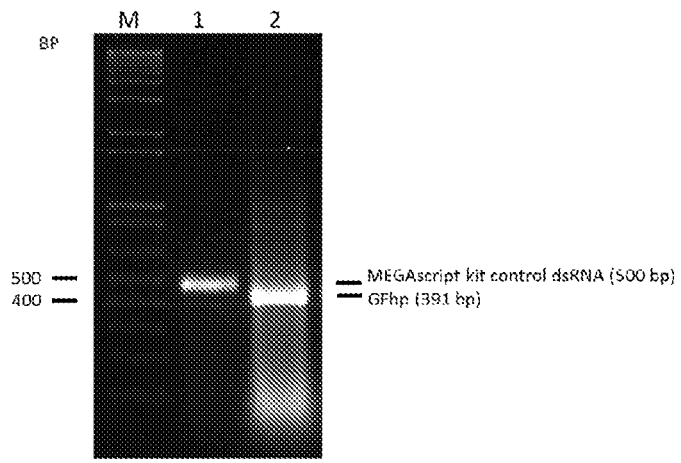
FIG. 5 is a gel electrophoresis of in vitro transcribed GF dsRNA.

The pGEM-GF hairpin vector was used for in vitro transcription and transformed into HT115. Only in vitro GF dsRNA was expressed and tested (FIG. 5). In FIG. 5, Lane 1 is in vitro transcribed kit control dsRNA; Lane 2 is in vitro transcribed GF dsRNA (391 bp); and M is 1 kb+ ladder. As with other in vitro transcribed dsRNA, a high yield (~1.5 µg/µL) of the GF dsRNA was obtained.

Detection of dsRNA

In vitro or in vivo expressed NIa, IR54 and GF dsRNA from respective vectors were assessed by dot blot hybridisation. Double-stranded RNA was placed on positively charged Nylon membranes (Roche Applied Science, Basel, Switzerland), cross-linked to membranes by GS GENE LINKER™ UV CHAMBER (BIO-RAD Laboratories, Hercules, Calif., U.S.A.) and pre-hybridised in 10 mL ULTRAhyb®-Oligo Hybridization Buffer (Life Technologies, Carlsbad, Mass., U.S.A.) for 1 hour at 38° C. in a HyBaid Shake 'n' Stack incubator. Expressed dsRNA was detected using oligonucleotide probes (Table 1) and DIG-labelled as per DIG Oligonucleotide 3'-End Labeling Kit, $2^{nd}$ Generation (Roche Applied Science, Basel, Switzerland). The chemiluminescent signal was captured from 1 hour up to 24 hours on Super RX (FujiFilm, Tokyo, Japan) and developed by Okamoto X3 Automatic film processor (KODAK, Rochester, N.Y., U.S.A.).

TABLE 1

Oligonucleotide sequences used

| Oligonucleotide Name | Sequence (5'3) | SEQ ID NO: |
|---|---|---|
| SP6 | ATTTAGGTGACACTATAG | 4 |
| T7 | TAATACGACTCACTATAGGG | 5 |
| NIa hairpin DIG | TCAGGAGAAGTATGCATCGTC | 6 |
| IR54 hairpin DIG | TGACATCGAAGACACCGCTTCT | 7 |
| Gf hairpin DIG | GAAGAAGTCGTGCTGCTTCATG | 8 |

Confirmation of NIa and IR54 dsRNA

Figure 6:
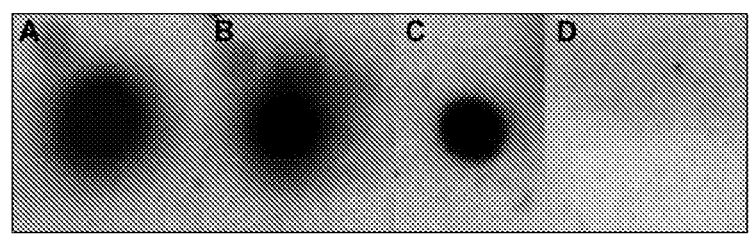
FIG. 6 is a RNA dot blot showing hybridisation of DIG-oligonucleotide probe to expressed NIa dsRNA at 2 hours exposure.
Figure 7:
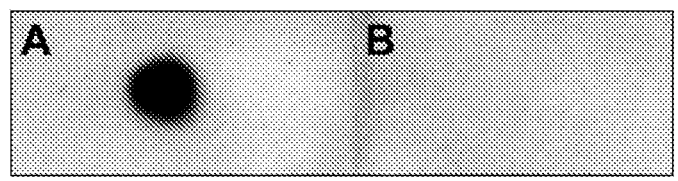
FIG. 7 is a RNA dot blot showing specific hybridisation of DIG-oligonucleotide probe to expressed IR54 dsRNA at 45 minutes exposure.

The expressed NIa and IR54 dsRNAs were analysed for complementarity to PVY or PMMoV by dot blot analysis using specific DIG-labelled oligonucleotide probes (FIGS. 6 and 7). In FIG. 6, Panel A is pGEM-NIa dsRNA in vitro transcribed; Panel B is L4440-NIa dsRNA induced in HT115; Panel C is L4440-NIa dsRNA in vitro transcribed; and Panel D is pGEM-IR54 dsRNA induced in HT115. In FIG. 7, Panel A is IR54 dsRNA induced in HT115; and Panel B is kit control dsRNA.

NIa dsRNA shows hybridisation with a PVY-specific probe (FIGS. 6 A, B and C), whereas the IR54 dsRNA utilised as a negative control does not bind to the PVY probe (FIG. 6D). Similarly, IR54 dsRNA probed with a PMMoV specific probe shows specific binding (FIG. 7A) whereas the negative control dsRNA (from the MEGAscript® RNAi kit) does not show any binding (FIG. 7B).

Confirmation of GF dsRNA

Figure 8:
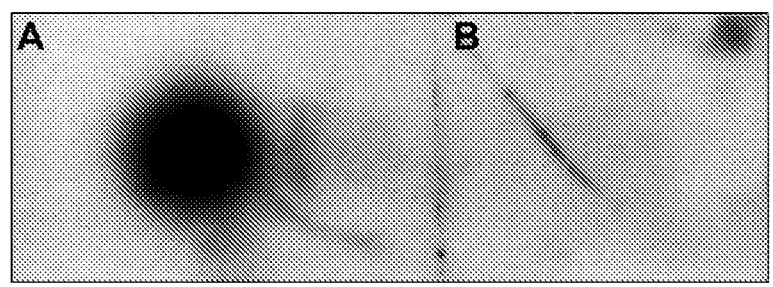
FIG. 8 is a RNA dot blot showing GF dsRNA sequence specificity to GFP DIG-oligonucleotide probe at 45 minutes exposure.

In vitro expressed GF dsRNA was tested for sequence complementarity by RNA dot blot analysis (FIG. 8). In FIG. 8. Panel A is GF dsRNA in vitro transcribed; and Panel B is Control dsRNA. GF dsRNA hybridised with GFP specific DIG-oligonucleotide probe (FIG. 8A), while the control dsRNA shows no chemiluminsence (FIG. 8B).

Example 2

Layered Double Hydroxide Nanoparticles

Figure 9:
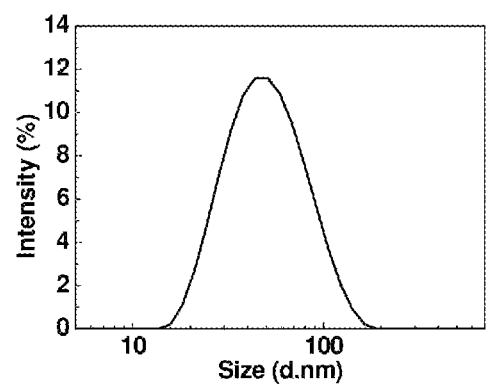
FIG. 9 illustrates the size distribution of LDH nanoparticles by Photon Correlation Spectroscopy (PCS)
Figure 10:
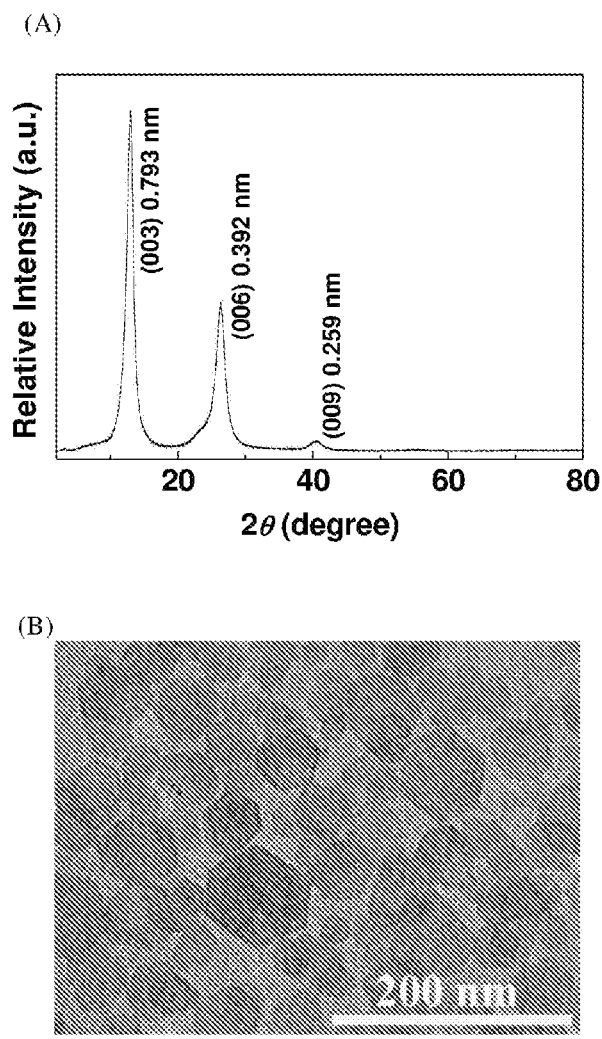
FIG. 10(A) provides the X-ray diffraction pattern of LDH nanoparticles and FIG. 10(B) provides microscopy images of LDH nanoparticles.

Small scale LDH of the formula $Mg_6Al_2(OH)_{16}CO_3.4H_2O$ were prepared using a non-aqueous co-precipitation method. Briefly, 10 mL of methanol solution containing 6 mM $Mg(NO_3)_2$ and 2 mM $Al(NO_3)_3$ was added drop wise to 40 mL methanol solution containing 16 mM NaOH under vigorous stirring for 10 minutes with $N_2$ bubbling. The mixture was then treated at 100° C. for 16 hours. The slurry was collected and washed twice with 20 mL deionized water via centrifugation, and then resuspended in 40 mL deionized water, resulting in an LDH suspension containing approximately 10 mg/mL homogeneously dispersed $Mg_3Al$-LDH nanoparticles (Chen et al., 2013). The characteristics of the resultant LDH nanoparticles is provided in Table 2, and the particle size, as measured by Photon Correlation Spectroscopy (PCS) using a Zetasizer Nano ZS (Malvern instruments, Worcestershire, U.K.), is illustrated in FIG. 9. LDH nanosheets were synthesised with an average lateral dimension of 120 nm and a thickness of 15-20 nm, combined together to form an average layer of 20-25 positively charged nanosheets (FIG. 10). In FIG. 10, Panel A is an X-ray diffraction (XRD) pattern of LDH nanoparticles and Panel B is a transmission electron microscopy (TEM) image of LDH nanoparticles.

TABLE 2

Characteristics and physical properties of LDH nanoparticles used in this study.

| Z-Ave (d · nm) | PdI | Intensity Mean (d · nm) | Number Mean (d · nm) | LDH concentration (mg/mL) |
|---|---|---|---|---|
| 34.1 | 0.217 | 44.20 | 12.11 | 10.55 |

LDH Analysis After Spray Application Onto Leaf Surface

Figure 11:
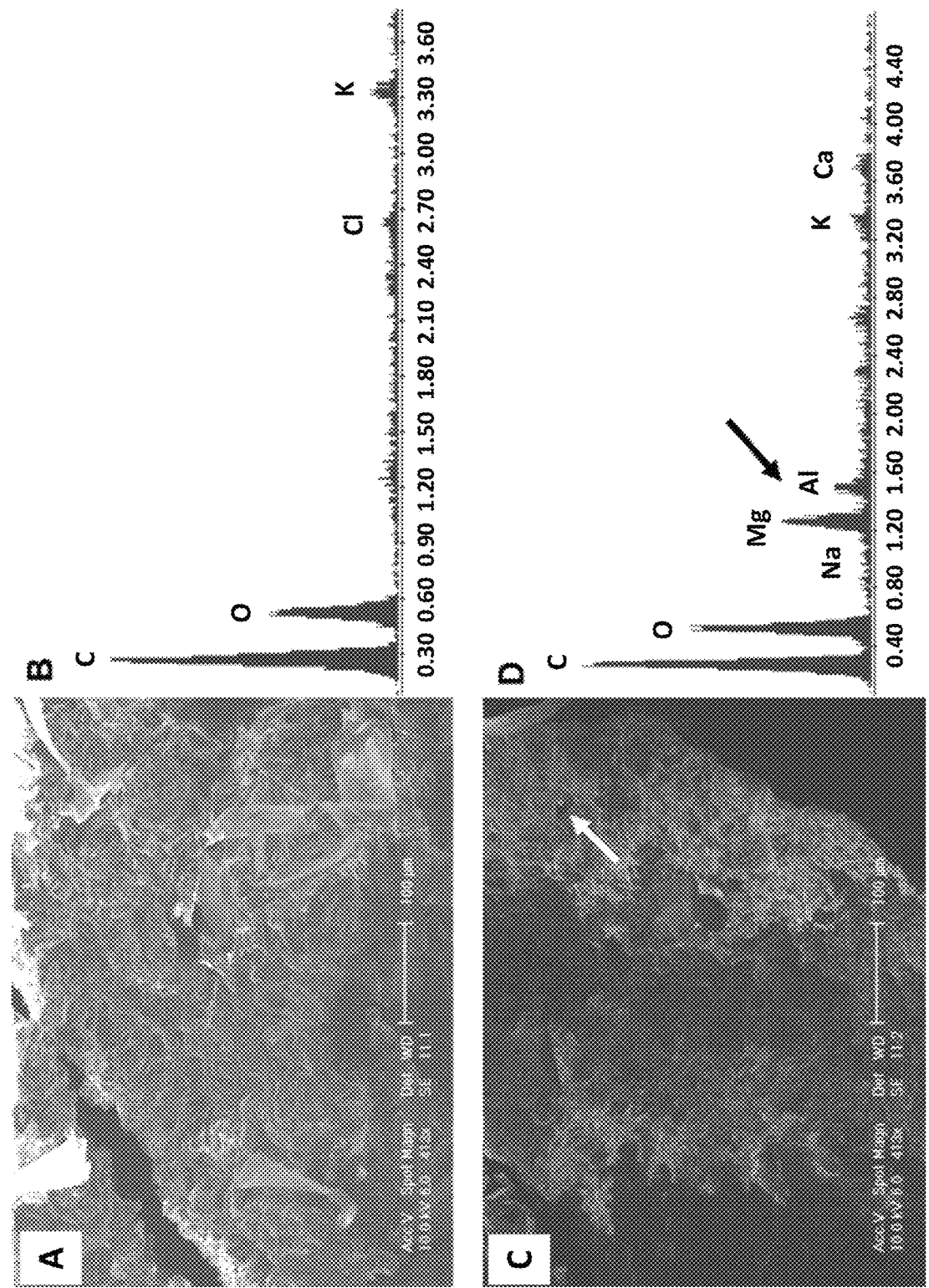
FIG. 11 provides the morphology of LDH when sprayed onto the surface of a leaf under Scanning Electron Microscope (SEM) and SEM-Dispersive Energy X-ray (DEX)

To define the maintenance of LDH morphology on leaves, 1 mL of LDH was sprayed onto a Nicotiana tabacum cv W38 (W38) leaf and compared with 1 mL of tap water for control. Samples were examined through Scanning Electron Microscope (SEM) and SEM-Dispersive Energy X-ray (DEX) observation. The morphology of the LDH is illustrated in FIG. 11. In this Figure, Panel A illustrates the W38 leaf sprayed with water under SEM; Panel B provides a Scanning Electron Microscope-Dispersive Energy X-ray (SEM-DEX) spectrum of leaf sprayed with water; Panel C illustrates the W38 leaf sprayed with LDH under SEM (arrow points to possible aggregate of LDH): and Panel D provides a SEM-DEX spectrum of leaf sprayed with LDH, showing an increased yield of Mg and Al ions indicating LDH presence.

The LDH nanosheets formed a uniform suspension when dissolved in water and could be sprayed easily onto the leaf. There was no visible difference by the naked eye between sprayed and unsprayed leaves and the plant retained all the normal growth characteristics.

ICP-Mass Spectrometry Assay for Stability of LDH

LDH Stability Upon Application onto Paper

An analysis of LDH breakdown was conducted on paper (a synthetic leaf) over a two-week period. The paper used was cut into 7 cm$^2$ pieces. LDH suspension (500 µL of 10.55 mg/mL-5.275 mg LDH) or water (500 µL) was spread onto the paper and maintained under glasshouse conditions. Samples were collected at day 0, 7, and 14. Samples were boiled in 10 mL of nitric acid. The boiling was conducted until approximately 2 mL of a clear pale yellow liquid remained. Samples were made up to a total volume of 10 mL with de-ionised water and sent to CaSS Forensic and Scientific Services (Brisbane, Australia) for Inductively Coupled Plasma Mass Spectrometry (ICP-MS) analysis of magnesium (Mg) and aluminium (Al) ions.

Figure 12:
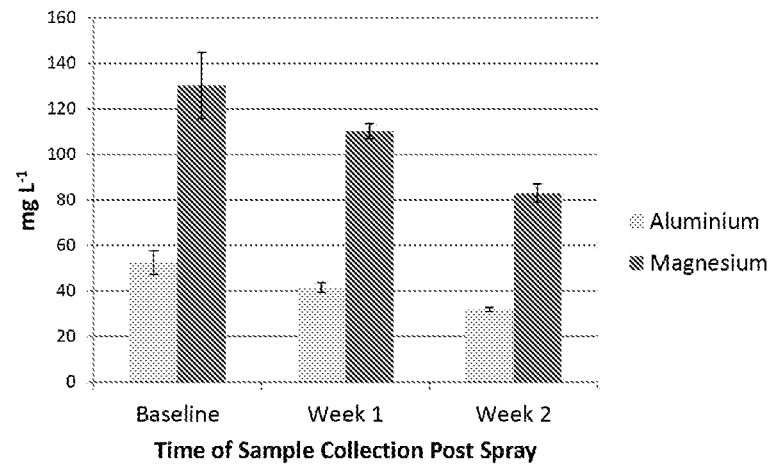
FIG. 12 provides Inductively Coupled Plasma Mass Spectrometry (ICP-MS) analysis of LDH breakdown over a two-week period when sprayed on a simulated leaf.
Figure 13:
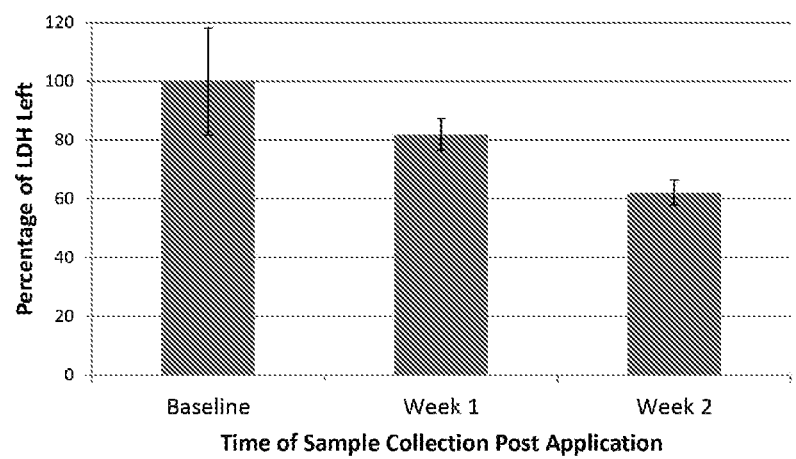
FIG. 13 provides the percentage of LDH remaining after application onto simulated leaves.

The analysis showed a gradual decrease from baseline over the two-week time frame (FIG. 12—bars represent the standard error about the mean). As expected, the baseline result was 49 mgL$^{-1}$ for Al (9.3%) and 131.875 mgL$^{-1}$ for Mg (25%). These results were used to calculate the percentage of LDH breaking down over the two-week period (FIG. 13—ICP-MS analysis results converted to percentage remaining; bars represent the standard error about the mean). In the first week an 18% drop was observed. A further 20% was observed between week one and two, indicating that 62% of the topically applied LDH still remained on the paper after two weeks. This indicates that the LDH will completely breakdown between 4-5 weeks (about 35 days).

Loading of dsRNA onto LDH

Different mass ratios were tested to optimise complete binding of dsRNA to LDH. LDH was loaded with MEGAscript® RNAi kit control dsRNA (control dsRNA) (500 bp) by incubating samples at 37° C. for 10 minutes with shaking (200 rpm). Double-stranded RNA (500 ng): LDH (500 ng) mass ratios were set at 2:1, 1:1, 1:2, 1:3, 1:4, 1:5 and 1:10 and resolved on a 1% agarose gel. Loading ratios were repeated with in vitro transcribed NIa, IR54 and GF dsRNA.

Figure 14:
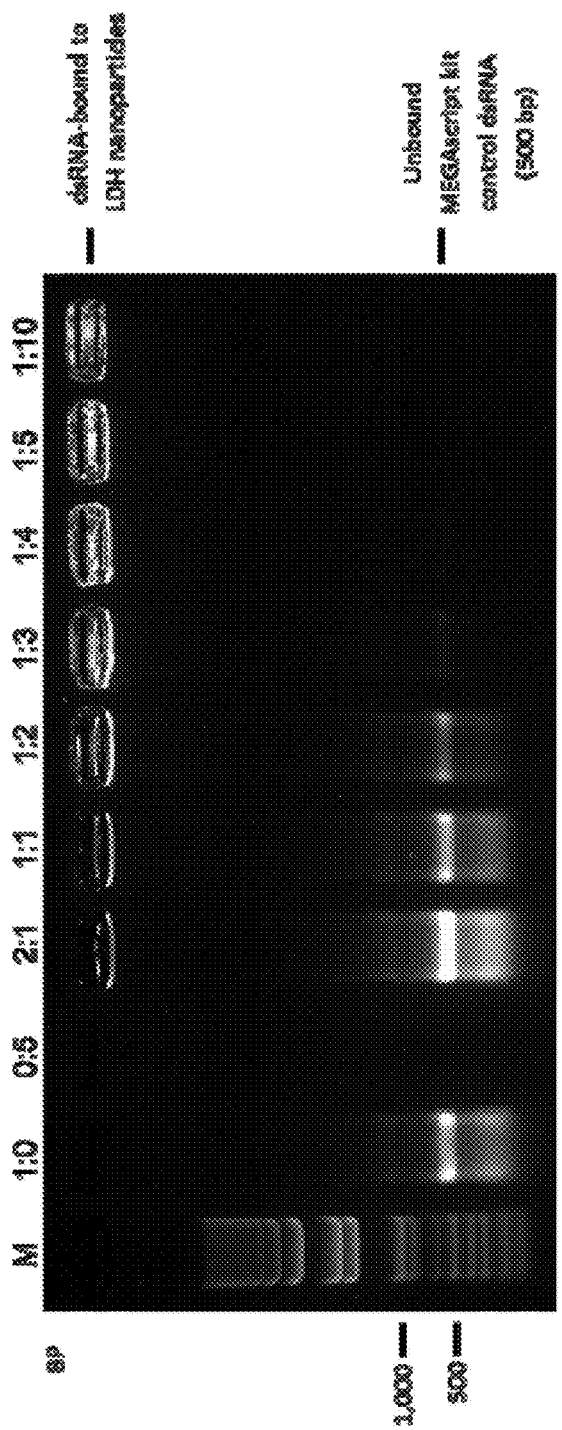
FIG. 14 provides a gel electrophoresis illustrating the loading mass ratios of 500 ng of control dsRNA onto LDH nanoparticles.
Figure 15:
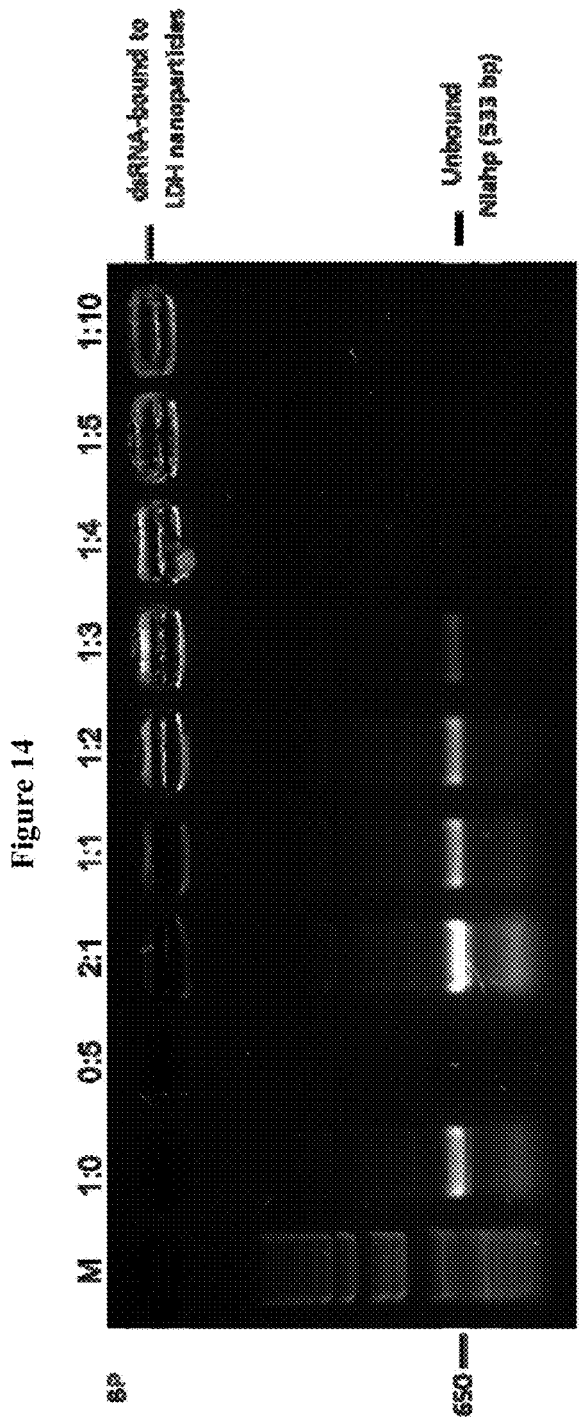
FIG. 15 provides a gel electrophoresis illustrating the loading mass ratio of 500 ng of NIa dsRNA (533 bp) onto LDH nanoparticles.
Figure 16:
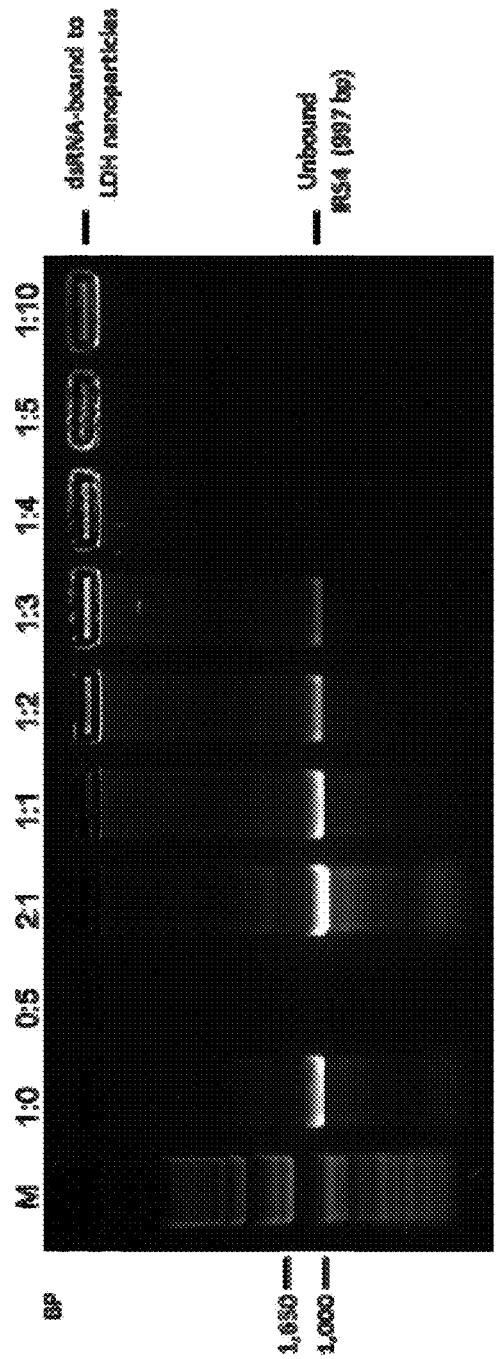
FIG. 16 provides a gel electrophoresis illustrating the loading mass ratios of 500 ng IR54 dsRNA (997 bp) onto LDH nanoparticles.
Figure 17:
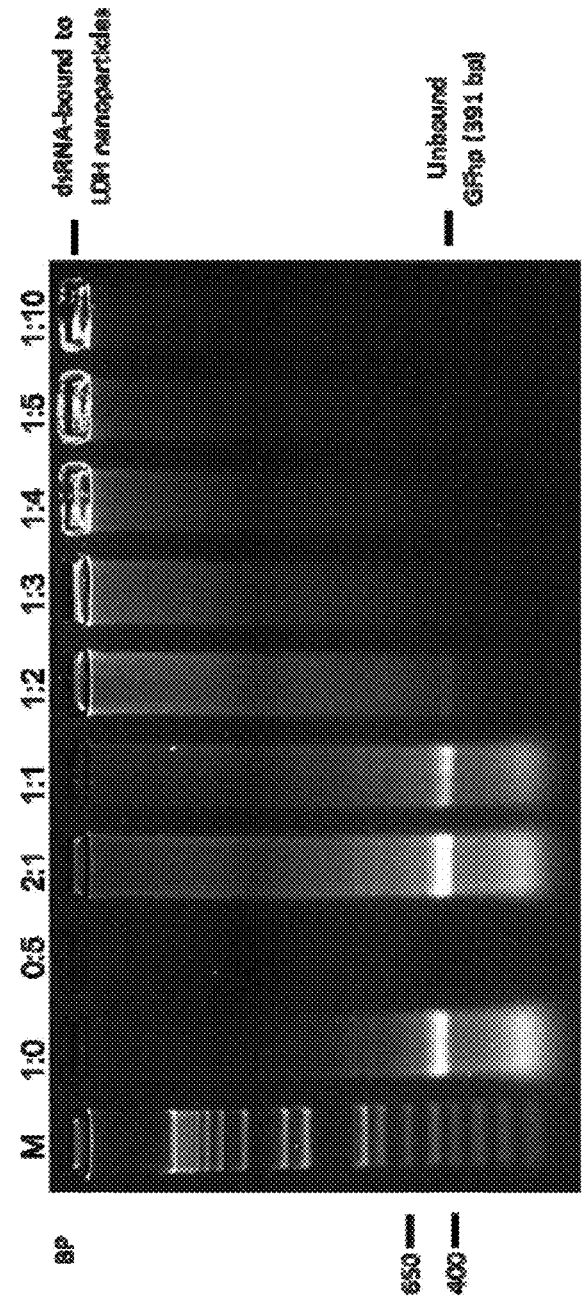
FIG. 17 provides a gel electrophoresis illustrating the loading mass ratios of 500 ng GF dsRNA (391 bp) onto LDH nanoparticles.

LDH-loading capacity of control dsRNA is illustrated in FIG. 14, of in vitro NIa dsRNA in FIG. 15, of in vitro IR54 dsRNA in FIG. 16 and of in vitro GF dsRNA in FIG. 17 (in these figures M=1 kb+ ladder). Gel electrophoresis revealed that once dsRNA is loaded onto LDH, it remains in the well and does not migrate, as can be seen by the florescence in the well, while the unbound dsRNA migrates into the gel. An example of complete loading can be seen in FIG. 14 mass ratios 1:4 and higher, while both bound and unbound dsRNA can be observed for ratios 1:3 and lower. Complete loading varied slightly between each construct, where control dsRNA, 533 bp NIa dsRNA and 997 bp IR54 dsRNA were completely bound at 1:4 mass ratio (FIGS. 14-16) while 391 bp GF dsRNA was completely bound by LDH at 1:3 mass ratio (FIG. 17).

Double-Stranded RNA Release from LDH nanoparticles

As proof of the binding of dsRNA to LDH, a quick artificial release was conducted by mixing the control dsRNA-loaded LDH nanoparticles (dsRNA:LDH ratio=1:3) 10 µL suspension with 30 µL of 1 M NaCl for 20 minutes to precipitate the dsRNA-bound and free LDH nanoparticles from solution and centrifuged at 14,000 rpm for 30 min. The supernatant was removed and checked on a 1% agarose gel for presence/absence of dsRNA while the pellet was resuspended in solutions with pH from 1.0 to 14.0 made with nitric acid and NaOH solution. Samples were resolved in 1% agarose. Double-stranded RNA release was visible in the pH 2.0 solution, so a pH reading of the reaction was conducted for mathematical purposes. Thus, 5 mL of pH 2.0 NHO$_3$+1 M NaCl solution was added to 2.5 mL 1000 ng/µl LDH and 5 mL 1 M NaCl. The pH was read after 0, 3, 10, 30 and 60 minutes.

Figure 18:
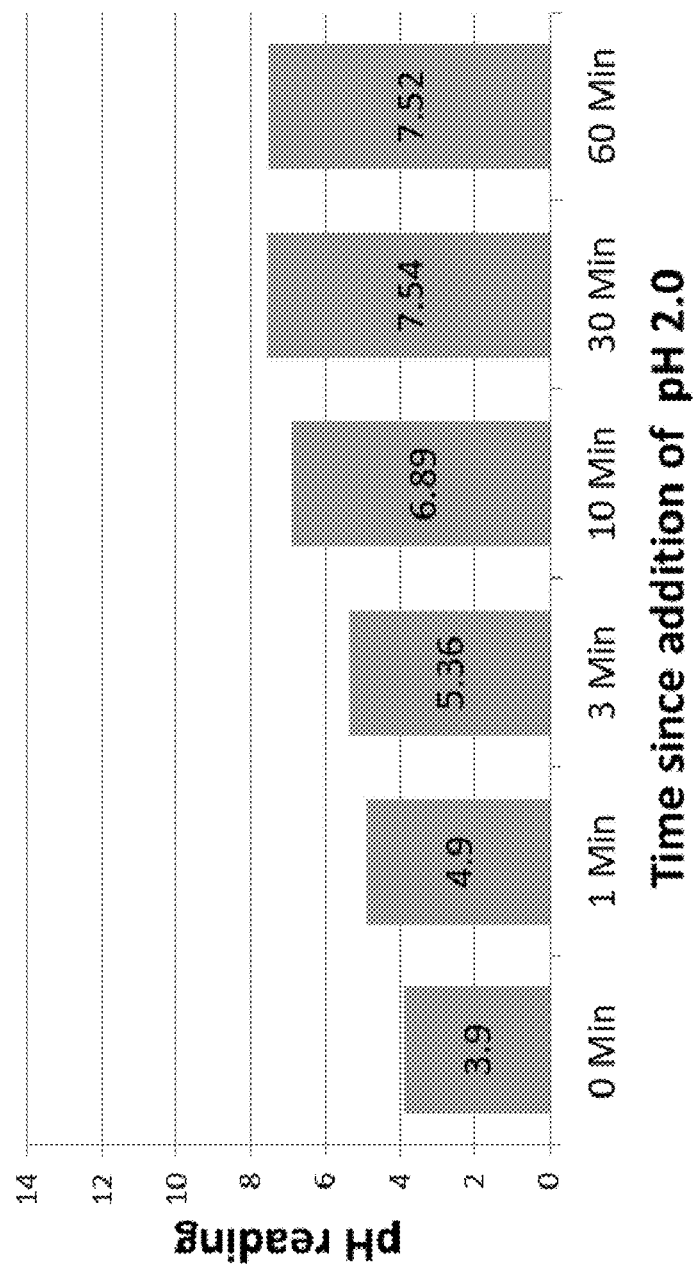
FIG. 18 illustrates the pH reading of control dsRNA-loaded LDH after the addition of nitric acid and NaCl (pH 2.0)

The initial acidic solution was neutralised as the LDH broke down (releasing Mg$^{2+}$ ions as well as H$_2$O and Al(OH)$_3$), as illustrated in FIG. 18 in which the initial pH measurement of 3.9 quickly changed in the first 2 minutes and balanced out at pH 7.52 after 1 hour. This analysis shows that pH 2.0 should release dsRNA, however a pH profile ranging from pH 1.0 to 14.0 was further analysed.

Figure 19:
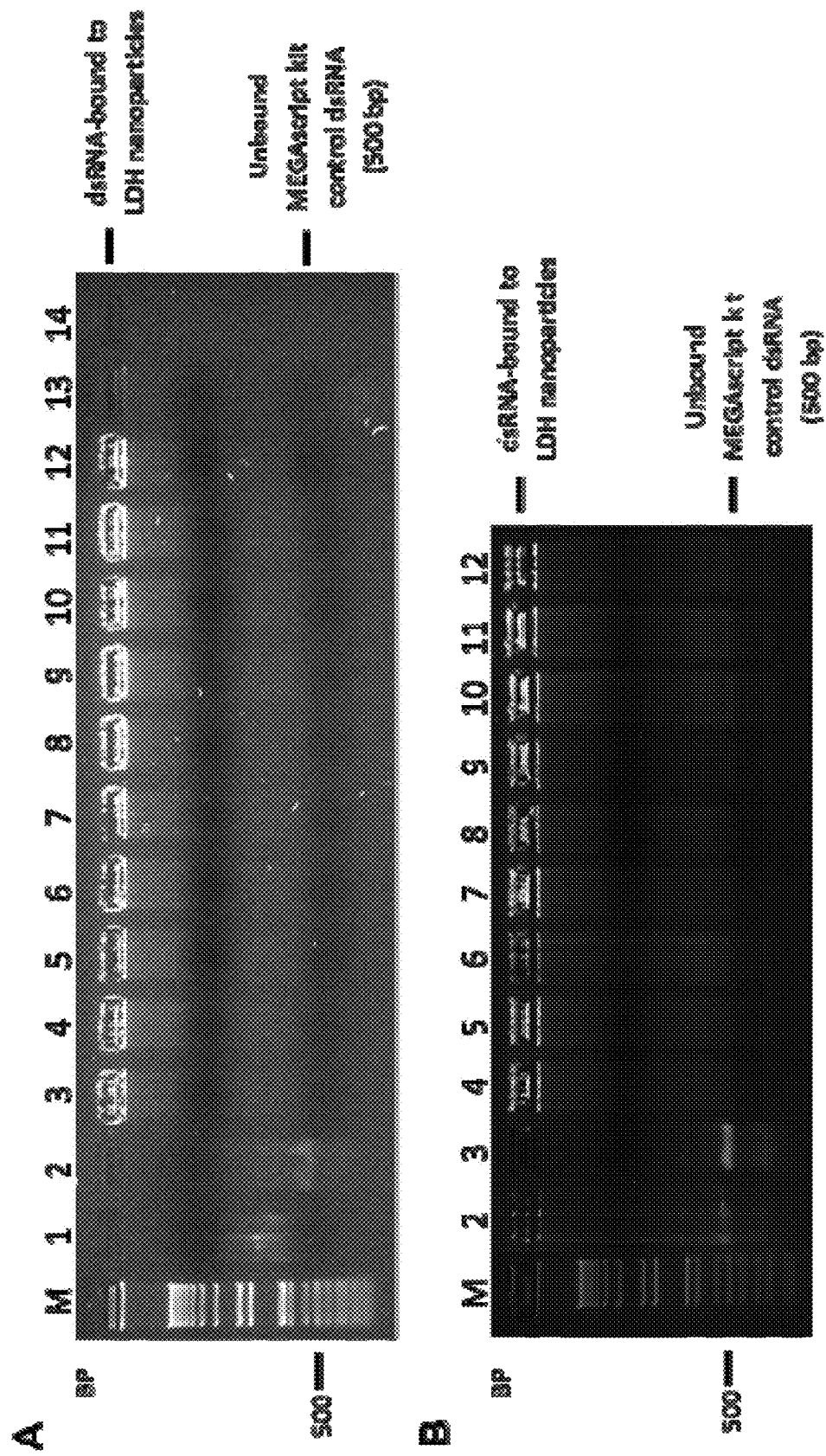
FIG. 19 illustrates the pH release profile of 1:3 control dsRNA-loaded LDH.

An artificial pH release profile of 1:3 control dsRNA: LDH was conducted by the addition of NaCl to precipitate dsRNA-bound and unbound LDH from solution. The pellet was resuspended in solutions ranging from pH 1.0 to 14.0 and resolved by gel electrophoresis immediately or after 1, 8 or 24 hours incubation at room temperature (FIG. 19). In FIG. 19, Panel A illustrates the immediate resolution of dsRNA-LDH after resuspension in pH solutions (1.0-14.0); and Panel B illustrates the resolution of dsRNA-LDH after 24 hour incubation in pH solutions (1.0-14.0) (M=1 kb+ ladder).

Resuspension at a pH of either 1.0 or 2.0 immediately released dsRNA (FIG. 19A), while 24 hour incubation in pH 3.0 also released dsRNA (FIG. 19 B). No release was observed at alkaline pH. The dsRNA-LDH resuspension in pH 13.0 and pH 14.0 would not load into the agarose gel loading well and therefore could not be resolved.

Figure 20:
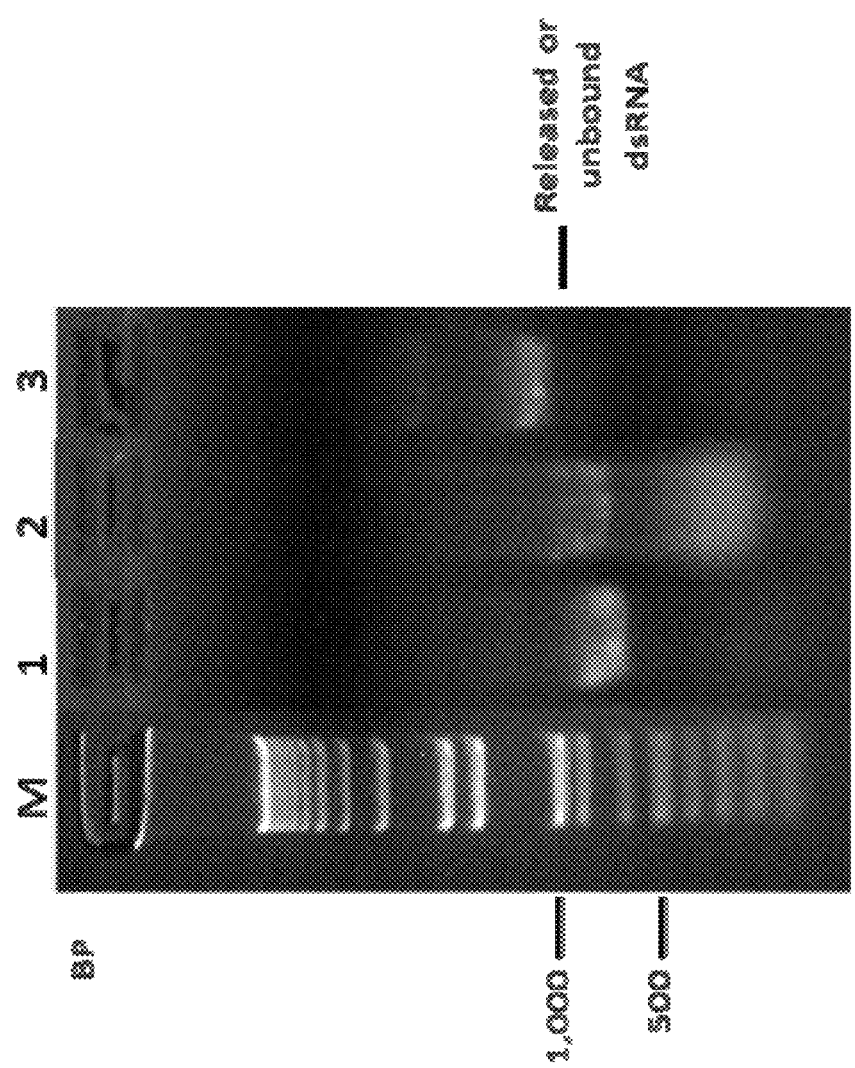
FIG. 20 provides a gel electrophoresis of nitric acid release (pH 2.0) of various double-stranded RNA from LDH.

Confirmation of dsRNA release from LDH was also conducted with 1:3 in vitro transcribed NIa dsRNA-, HT115 expressed NIa dsRNA, and IR54 dsRNA loaded LDH using the pH 2.0 solution. The release of this dsRNA was resolved on a 1% agarose gel (FIG. 20). In FIG. 20, Lane 1 is in vitro transcribed NIa dsRNA released from LDH with pH 2.0 solution; Lane 2 HT115 expressed NIa dsRNA released from LDH with pH 2.0 solution; Lane 3 is HT115 expressed IR54 dsRNA released from LDH with pH 2.0 solution; M=1 kb+ ladder, Shelf-Life Storage of dsRNA-Loaded into LDH Nanoparticles The stability of two sets of 1:3 dsRNA-loaded nanoparticles (control dsRNA: LDH=500 ng; 1500 ng) were tested in triplicate over a period of 60 days when stored in 1.5 mL tubes. Samples were stored in four different conditions of either light or dark and either sterile DEPC treated water or non-sterile tap water. Dark, sterile samples were analysed at 0, 3, 7, 10, 20, 30 and 60 days. Both light and dark non-sterile samples were analysed at 1, 5, 10, 30 and 60 days while light sterile was analysed at 10, 30 and 60 days. One set of 1:3 dsRNA-loaded LDH was artificially released as per the above with pH 2.0. The stability of the dsRNA-loaded nanoparticles was assessed by gel electrophoresis (1% agarose gel).

Figure 21:
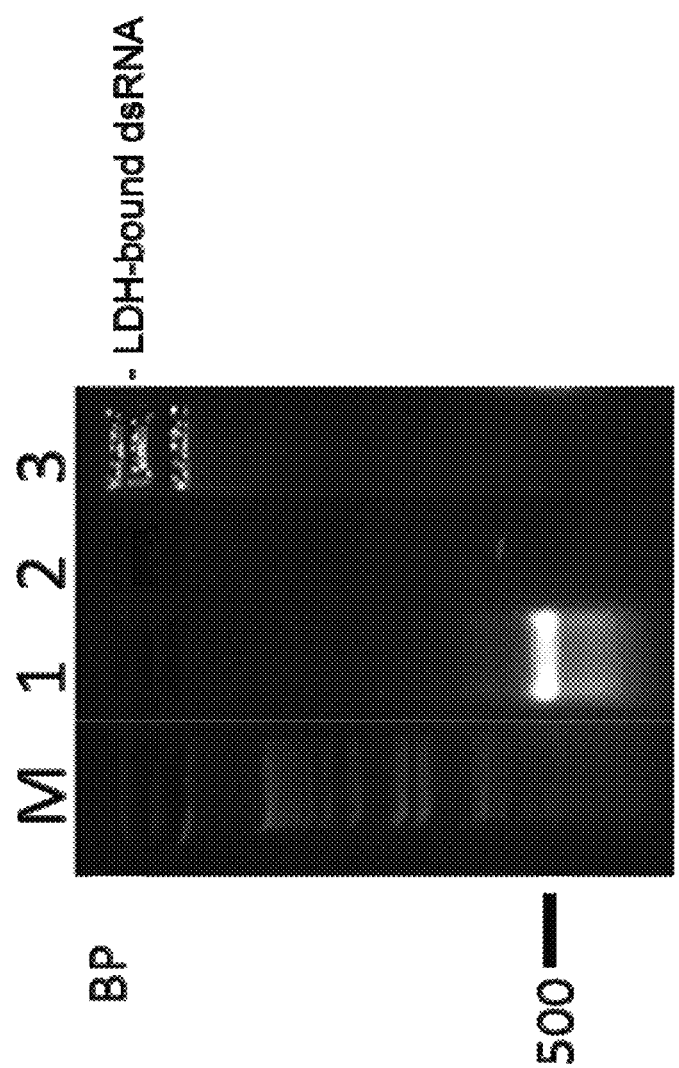
FIG. 21 provides a gel electrophoresis illustrating the stability of dsRNA-loaded LDH.

LDH-bound dsRNA was found to be stable even after storage for 60 days, regardless of whether the LDH-bound dsRNA was stored with sterile or non-sterile water or under light or dark conditions. No degradation was observed of the LDH-bound dsRNA by gel electrophoresis (FIG. 21). In FIG. 21 Lane 1 is fresh 500 ng of in vitro transcribed NIa dsRNA; Lane 2 is 2.5 µg LDH suspended in non-sterile water and stored in light for 60 days; Lane 3 is 1:5 in vitro transcribed NIa dsRNA:LDH suspended in non-sterile water and stored in light for 60 days; and M is the 1 kb+ ladder.

Protection of dsRNA-Loaded into LDH Nanoparticles

Figure 22:
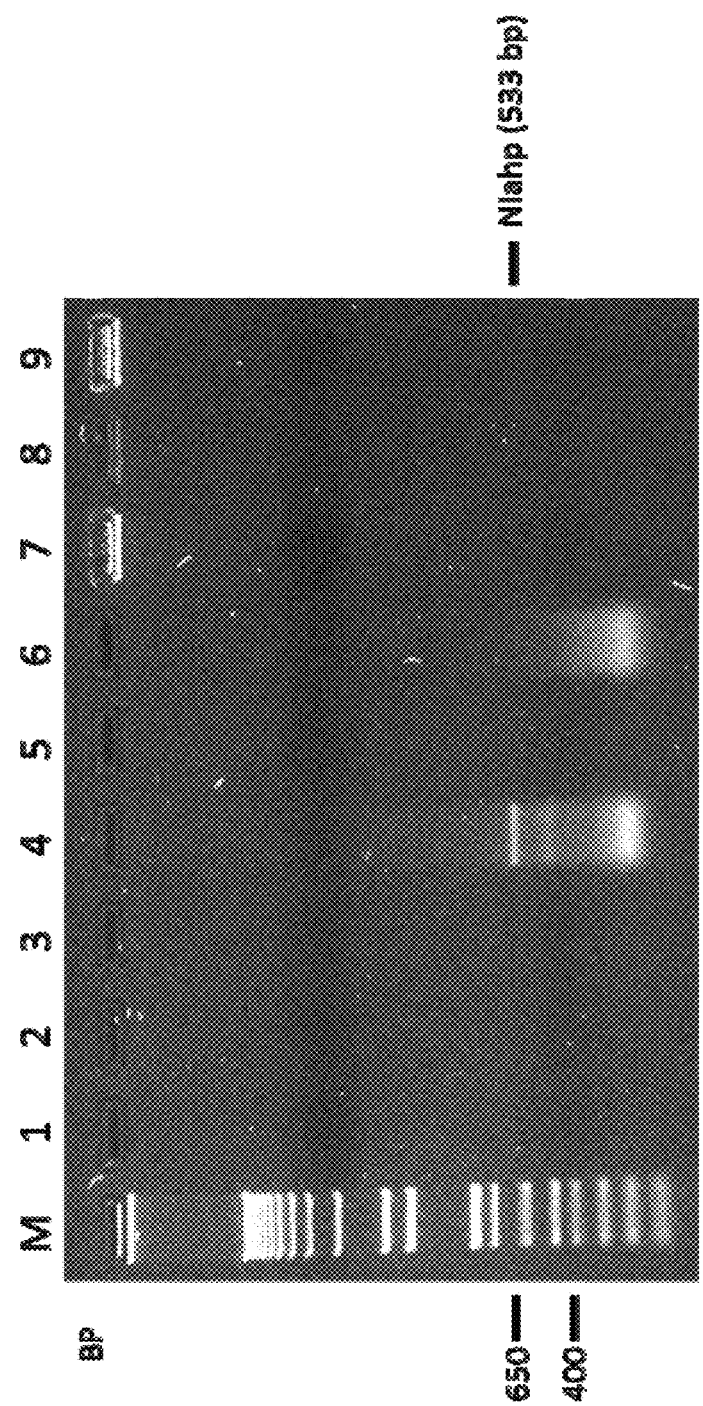
FIG. 22 provides a gel electrophoresis illustrating LDH's ability to protect dsRNA from detrimental environmental factors (such as RNase and UV light)

LDH's ability to encapsulate the dsRNA and protect it from detrimental environmental factors (such as RNase and UV light) was examined. In this experiment. 2.5 µg LDH, HT115 expressed 'naked' NIa dsRNA (500 ng) and 1:5 NIa dsRNA LDH were either: (i) incubated at 37° C. for 20 min with 1 ng of RNase A; or (ii) placed under a UV lamp for 8 hours. FIG. 22 shows that the RNase A treatment completely degraded the 'naked' NIa dsRNA (FIG. 22. Lane 5), while the NIa dsRNA:LDH shows protection (FIG. 22, Lane 8). Samples exposed to UV showed complete degradation of 'naked' NIa dsRNA while some degraded RNA remained (FIG. 22, Lane 6). NIa dsRNA LDH exposed to UV light (FIG. 22, Lane 9) showed no degradation in comparison to the untreated NI a dsRNA LDH (FIG. 22, Lane 7). In FIG. 22 Lane 1 is untreated LDH: Lane 2 is RNase A treated LDH; Lane 3 is UV treated LDH; Lane 4 is untreated NIa dsRNA: Lane 5 is RNase A treated NIa dsRNA: Lane 6 is UV treated NIa dsRNA; Lane 7 is untreated 1:5 NIa dsRNA: LDH: Lane 8 is RNase A treated 1:5 NIa dsRNA:LDH; Lane 9 is UV treated 1:5 NIa dsRNA:LDH: and M is 1 kb+ ladder.

Example 3

Topical Application of dsRNA:LDH on Plants

Analysis of Spray Application Jar Treatments

The following experiments required spray application of treatments (water, dsRNA, LDH or dsRNA-loaded LDH) onto either the leaf or entire plant. To quantify the amount of liquid released per spray, bottles were filled with water and sprayed into weigh boats. Weight per spray was recorded and converted from g to mL.

Viral Inoculum for Challenge Experiments

The PMMoV inoculum was a kind gift from Dr Geering, QAAFI as an infected leaf sample. PVY inoculum was available in the Mitter laboratory. The viral inoculum was multiplied by mechanical inoculation on either *N. benthamiana* or W38. Briefly, the infected leaves were ground in 5 mM potassium phosphate buffer, pH 7.5. The leaves to be inoculated were dusted with carborundum powder and then gently rubbed with the ground sap carrying the virus. Symptoms were recorded at 3-15 days post inoculation (dpi).

ELISA (Enzyme-Linked Immunosorbant Assay)

The virus titre in the inoculated and systemic leaves (non-inoculated new leaves) where applicable was determined by ELISA kit specific to each virus (Agdia, Elkhart, Ind., U.S.A.) as per manufacture's protocol using three 8 mm discs randomly picked from the leaf sample. Plates were read using PowerWave Xs (Bin Tex, Winooski, Vt., U.S.A.) plate reader at 405 nm. The absorbance value was used as indicator of virus titre.

PMMoV Protection Experiments

Co-Inoculation of PMMoV Virus and IR54 dsRNA Spray

The standard viral inoculum used was one 8 mm cut-out disc of PMMoV infected *N. benthamiana* leaf homogenised in 1 mL of 5 mM potassium phosphate buffer, diluted to 1:500 or 1:100.

The leaves of hypersensitive, local lesion host *N. tabacum* cv. Xanthi nc was used to analyse the effectiveness of dsRNA to silence PMMoV infection. Leaves were challenged with PMMoV only on the left-hand side, while the right-hand side was challenged with PMMoV after treatment of either 'naked' IR54 dsRNA, LDH alone or 1:2.5 IR54 dsRNA:LDH. The dsRNA concentration used was 1 µg per leaf. The viral inoculum used was diluted to 1:100. Three leaves were used for each treatment, with viral lesions recorded at 3 dpi.

Figure 23:
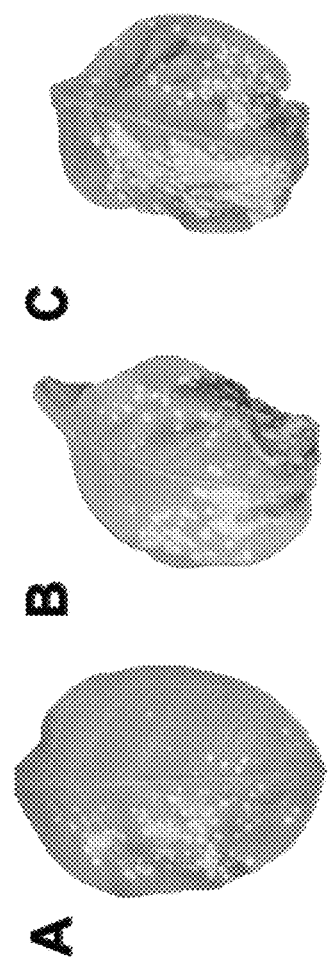
FIG. 23 provides photographs of hypersensitive *N. tabacum* cv Xanthi nc photographed 3 days after PMMoV inoculation.

The results are provided in FIG. 23 and Table 3. In FIG. 23, photograph A is right-half 'naked' IR54 dsRNA+PMMoV; left-half PMMoV only, Photograph B is right-half LDH only+PMMoV; left-half PMMoV only, Photograph C is right-half 1:2.5 IR54 dsRNA:LDH+PMMoV; left-half PMMoV only. It was observed that 'naked' IR54 dsRNA reduced lesions in comparison to PMMoV only (FIG. 23A), while LDH alone (FIG. 23B) did not cause much reduction (Table 3). IR54 dsRNA:LDH shows a slight reduction in local lesions but requires optimisation (FIG. 23C).

TABLE 3

Average number of local lesions on a hypersensitive host infected with PMMoV and treated with IR54 dsRNA and LDH nanoparticles.

| | PMMoV/ water only | PMMoV/ PMMoV + IR54 dsRNA | PMMoV/ PMMoV + LDH | PMMoV/PMMoV + 1:2.5 IR54 dsRNA:LDH |
|---|---|---|---|---|
| Average no. of lesions | 29/1 | 53/13 | 34/35 | 61/46 |

Figure 24:
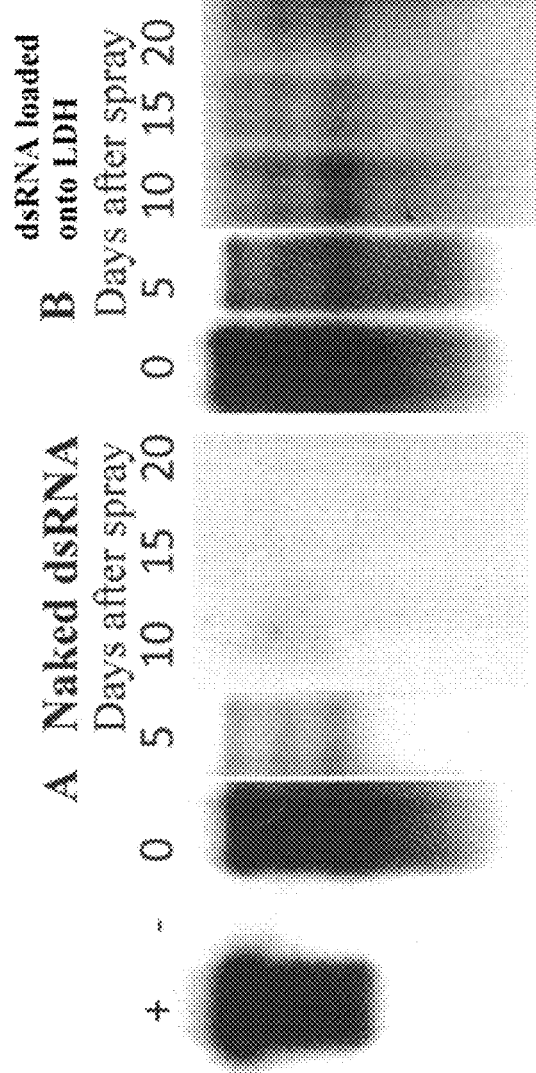
FIG. 24 provides northern blot analysis of IR54 dsRNA or IR54 dsRNA loaded onto LDH over time when applied to a leaf.

Stability of dsRNA versus dsRNA:LDH was tested on *Nicotiana tabacum* cv Xanthi leaves. Leaves were sprayed with 'naked' IR54 dsRNA and 1:2 IR54 dsRNA:LDH up to a total volume of 500 µL. The concentration of dsRNA used was 1 µg per leaf. Samples were collected at days 0, 5, 10, 15 and 20 after spraying and total RNA was loaded onto a PAGE-gel for Northern blot analysis. Northern blot analysis of the leaves showed that 'naked' IR54 dsRNA was almost completely degraded 10 days after spraying. In contrast, the IR54 dsRNA:LDH was much more stable, and still detected 20 days after spraying (see FIG. 24), In FIG. 24, + is dsRNA (positive control) and − is unsprayed leaves (negative control).

Time Course Experiment for PMMoV Protection

It was found that 1:100 dilution of PMMoV was too concentrated, as lesions coalesced together making it hard to count individual lesions (FIG. 23). As a result, time course analysis used a 1:500 dilution of the inoculum that was applied onto the full leaf.

The leaves of hypersensitive host *N. tabacum* cv. Xanthi nc were sprayed with water only or 1:2 IR54 dsRNA:LDH on day 0 and inoculated with PMMoV at 0, 5, 10, 15 and 20 days after the spray. The dsRNA concentration used was 1 μg per leaf. In this experiment, the ratio of dsRNA:LDH used was 1:2 as at that ratio the dsRNA does not bind completely to LDH and therefore some of it will be available as free dsRNA (FIG. 16). Also the inoculum used was diluted to 1:500. The experiment was done with three leaves for each treatment at each time point. Plants were photographed and local lesions counted at 6 dpi. LDH alone was not tested, due to confirmation of no protection from PMMoV (FIG. 23B).

Figure 25:
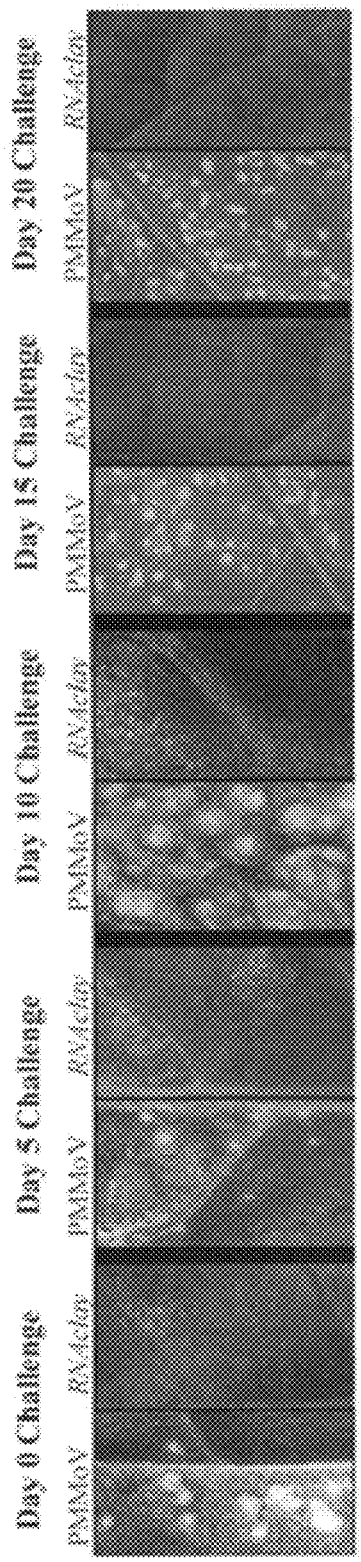
FIG. 25 provides photographs of *N. tabacum* cv. Xanthi which have been sprayed with either water (PMMoV photos) or IR54 dsRNA (RNAclay photos) and then challenged with PMMoV 0, 5, 10, 15 or 20 days after the spray.

A reduction in lesions was observed in leaves co-inoculated with IR54 dsRNA:LDH at day 0 (FIG. 25). A similar observation can be made with leaves challenged with PMMoV 5, 10, 15 and 20 days after spraying IR54 dsRNA: dsRNA (FIG. 25). LDH-loaded IR54 dsRNA were able to provide protection up to 20 days after application (FIG. 25). In FIG. 25, the hypersensitive host *N. tabacum* cv Xanthi nc is challenged with PMMoV at days 0, 5, 10, 15 and 20 of treatment. All plants were photographed 6 days after PMMoV inoculation.

PVY Protection Experiments

Co-Inoculation of PVY Virus and NIa dsRNA Spray

The standard inoculum used was one 8 mm cut-out disc of PVY infected W38 leaf homogenised in 1 mL of 5 mM potassium phosphate buffer, diluted to 1:1000.

Figure 26:
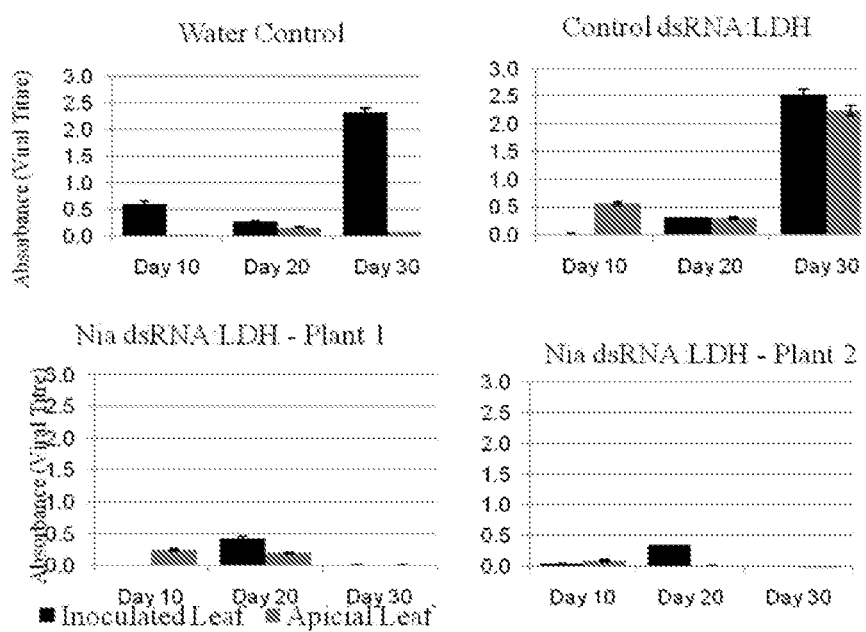
FIG. 26 provides a graph illustrating the results of ELISA detection of PVY in plants co-inoculated with PVY and various other agents.

The leaves of W38 were treated with water only, 1:5 control dsRNA:LDH or 1:5 NIa dsRNA:LDH. Plants were challenged with PVY on the same day (FIG. 26). The dsRNA concentration was 500 ng per leaf. Two leaves on a single plant were sprayed with water and 1:5 control dsRNA:LDH, while two leaves on two plants were sprayed with 1:5 NIa dsRNA:LDH. Both the inoculated leaf and an apical or systemic leaf were analysed by PVY-specific ELISA.

FIG. 26 provides the results of ELISA detection of PVY in treated plants challenged with PVY, illustrating the results of co-inoculation of PVY and water (Water Control), control dsRNA:LDH (Control dsRNA:LDH), and 1:5 NIa dsRNA: LDH (NIa dsRNA:LDH-Plant 1 and NIa dsRNA:LDH-Plant 2).

Plants sprayed with 1:5 NIa dsRNA:LDH and challenged with PVY showed a reduced viral titre when challenged immediately after spraying and no PVY could be detected at day 30 in both inoculated and systemic leaves (FIG. 26).

Time Course Experiment for PVY Protection

Entire four-leaf stage plants were sprayed with water only, LDH only, 'naked' NIa dsRNA or 1:2.5 NIa dsRNA:LDH on day 0. A concentration of 1 μg of HT115 NIa dsRNA was used per plant. A mass loading ratio of 1:2.5 dsRNA:LDH was used to have some dsRNA available immediately upon spraying. The plants were inoculated with PVY (1:1000 dilution) at 3 days after the spray. The 1:1000 diluted viral inoculum was mechanically inoculated onto two leaves. PVY symptoms were observed and ELISA samples were collected at 10 and 20 dpi. Plants were grown in glasshouse conditions of an average temperature of 25-26° C. (minimum temperature of greater than 23° C. and a maximum temperature of less than 29° C. (typically less than 27° C.)).

Figure 27:
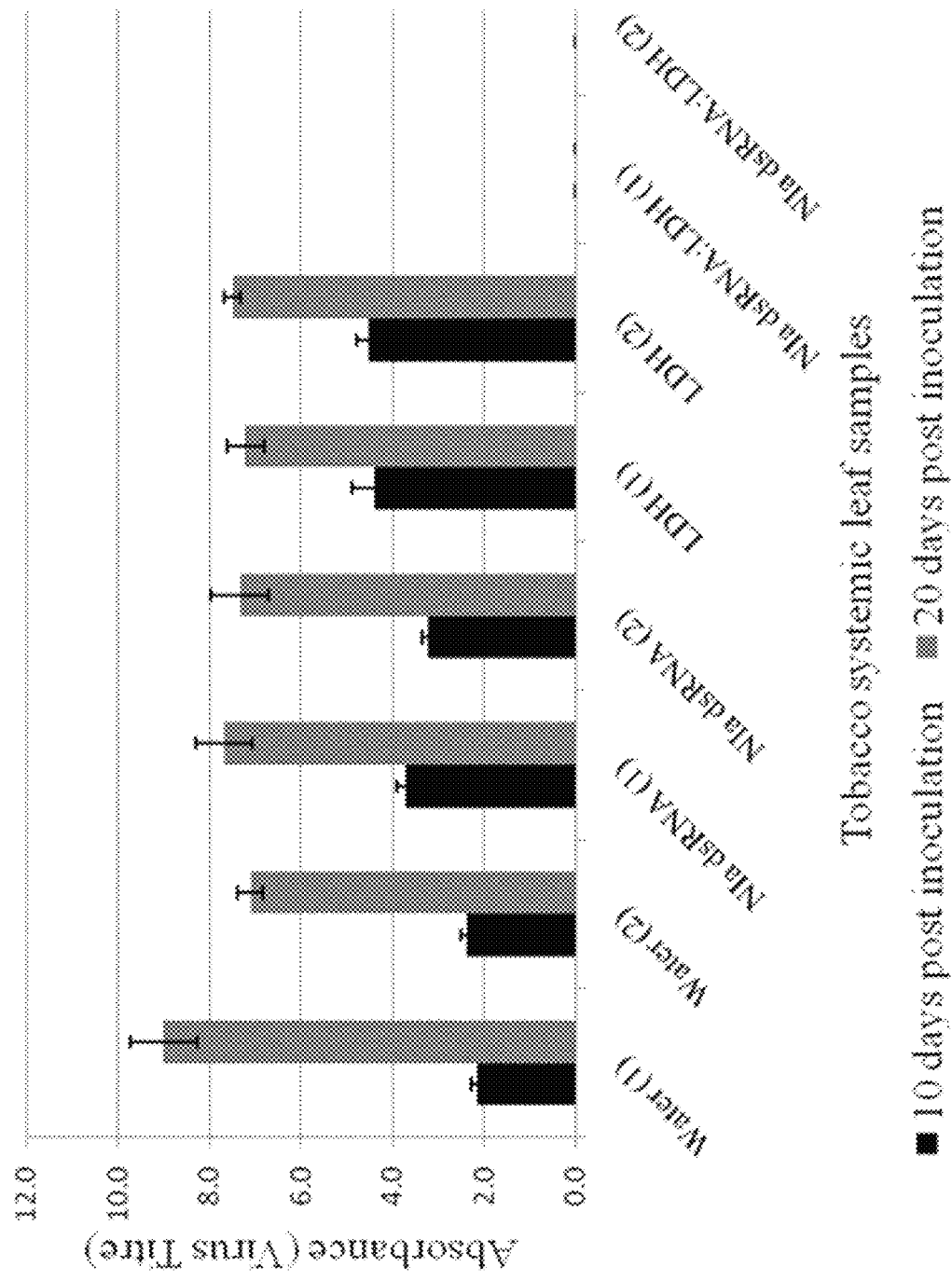
FIG. 27 provides a graph illustrating the results of ELISA detection of PVY in plants challenged with PVY 3 days after being sprayed with various other agents.

The results of the experiment for two replicate plants per treatment are provided in FIG. 27. PVY was detected at days 10 and 20 in plants sprayed with water, LDH only and 'naked' NIa dsRNA. Plants sprayed with 1:2.5 dsRNA:LDH and challenged with PVY 3 days later, recorded no virus in inoculated or systemic leaves (FIG. 27). These results indicate that 'naked' NIa dsRNA was degraded on the leaves within 3 days of application, while NIa dsRNA:LDH protected the NIa dsRNA from degradation and conferred resistance to PVY.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

CITATION LIST

Brosnan, C., N. Mitter, M. Christie, N. Smith, P. Waterhouse & B. Carroll, (2007) Nuclear gene silencing directs reception of long-distance mRNA silencing in Arabidopsis. *Proceedings of the National Academy of Sciences* 104: 14741-14746.

Chen, M., H. M. Cooper, J. Z. Zhou, P. F. Bartlett & Z. P. Xu, (2013) Reduction in the size of layered double hydroxide nanoparticles enhances the efficiency of siRNA delivery. *Journal of Colloid and Interface Science* 390: 275-281.

Gan, D., J. Zhang, H. Jiang. T. Jiang, S. Thu & B. Cheng, (2010) Bacterially expressed dsRNA protects maize against SCMV infection. *Plant Cell Reports* 29: 1261-1268.

Gleave, A. P., (1992) A versatile binary vector system with a T-DNA organisational structure conducive to efficient integration of cloned DNA into the plant genome. *Plant Molecular Biology* 20: 1203-1207.

Mills, S. J., A. G. Christy, J.-M. R. Génin. T. Kameda, & F. Colombo, (2012) Nomenclature of the hydrotalcite supergroup: natural layered double hydroxides. *Mineralogical Magazine* 76: 1289-1336.

Mitter, N. & R. G. Dietzgen, (2012) Use of hairpin RNA constructs for engineering plant virus resistance. *Methods Molcular Biology* 894: 191-208, Mitter, N., R. Mitchell & R. G. Dietzgen, (2006) Fate of hairpin transcript components during RNA silencing and its suppression in transgenic virus-resistant tobacco. *Journal of Biotechnology* 126: 115-122.

Mitter, N., E. Sulistyowati & R. G. Dietzgen, (2003) Cucumber mosaic virus infection transiently breaks dsRNA-induced transgenic immunity to Potato virus Y in tobacco. *Molecular Plant-Microbe Interactions* 16: 936-944.

Tenllado, F. & J. R. Diaz-Ruiz, (2001) Double-stranded RNA-mediated interference with plant virus infection. *Journal Virology* 75: 12288-12297.

Tenllado, F., B. Martínez-García, M. Vargas & J. R. Díaz-Ruíz, (2003) Crude extracts of bacterially expressed dsRNA can be used to protect plants against virus infections. *Biomedicalcentral Biotechnology* 3: 3.

Timmons, L. & A. Fire, (2001) Ingestion of bacterially expressed dsRNAs can produce specific and potent genetic interference in *Caenorhabditis elegans*. *Gene* 263: 103-112.

The invention claimed is:

1. A method for protecting a plant from an organism, comprising administering to the plant an effective amount of an RNAi composition comprising double-stranded RNA adsorbed onto Layered Double Hydroxide (LDH) particles; wherein the double-stranded RNA comprises a nucleotide sequence which is complementary to a nucleotide sequence of an RNA expressed by the organism; wherein the organism is a plant virus, viroid, parasite, insect, nematode, fungus or oomycete.

2. The method of claim 1, wherein the double-stranded RNA comprises a nucleotide sequence which is complementary to a nucleotide sequence of an RNA expressed by a plant virus or viroid.

3. The method of claim 1, wherein the double-stranded RNA is from 80 to 1500 base pairs in length.

4. The method of claim 1, wherein administering comprises spraying the composition onto the leaves of the plant.

5. The method of claim 1, wherein the LDH is represented by formula (1)

$$M^{II}_{1-x}M^{III}_{x}(OH)_2A^{n-}_{x/n}.yH_2O \quad (1)$$

wherein $M^{II}$ represents di-valent metal ions;

$M^{III}$ represents tri-valent metal ions;

$A^{n-}$ represents the interlayer anion of valance n;

x represents the proportion of trivalent metal to the total amount of metal ion present;

y represents variable amounts of interlayer water.

6. The method of claim 5, wherein the LDH is represented by formula (2)

$$M^{II}_{n}M^{III}(OH)_{2(n+1)}X.yH_2O \quad (2)$$

wherein X is one or more anions or negatively charged material to balance charge in the hydroxide layer.

7. The method of claim 5, wherein $M^{II}$ is at least one selected from the group consisting of Mg, Fe, Co, Ni, Cu, Zn, Mn, Pd, Cd and Ca; and $M^{III}$ is at least one selected from the group consisting of Al, Co, Fe, Mn, Ga, Rh, Ru, Cr, V, In, Y, Gd, Ti and La.

8. The method of claim 1, wherein the double-stranded RNA comprises a second nucleotide sequence which is complementary to a nucleotide sequence of an RNA expressed by a second organism, wherein the second organism is a plant virus, viroid, parasite, insect, nematode, fungus or oomycete.

9. The method of claim 1, wherein the LDH is of the hydrotalcite group.

10. The method of claim 1, wherein the composition is in the form of a solid, suspension or colloid.

11. The method of claim 1, wherein the composition is in the form of a suspension or colloid.

12. The method of claim 11, wherein the suspension or colloid comprises the double-stranded RNA adsorbed onto Layered Double Hydroxide (LDH) particles at up to 5% w/w of the suspension or colloid.

13. The method of claim 1, wherein the double-stranded RNA (dsRNA) is loaded onto the LDH at a ratio of from 2:1 to 1:20 dsRNA:LDH.

14. The method of claim 1, wherein the double-stranded RNA (dsRNA) is loaded onto the LDH at a ratio of from 1:1 to 1:6 dsRNA:LDH.

15. The method of claim 1, wherein from 50% to 95% of the double-stranded RNA in the composition is adsorbed onto the LDH.

16. The method of claim 1, wherein the LDH particles have a largest dimension within the range of 20-400 nm.

17. The method of claim 1, wherein the double-stranded RNA comprises a nucleotide sequence which is complementary to a nucleotide sequence of an RNA expressed by the organism, wherein the organism is a plant virus, viroid, insect, nematode, fungus or oomycete.

* * * * *